United States Patent
Walter

(10) Patent No.: US 6,277,858 B1
(45) Date of Patent: Aug. 21, 2001

(54) PYRIMIDIN-4-ONE AND PYRIMIDIN-4-THIONE AS FUNGICIDE

(75) Inventor: Harald Walter, Rodersdorf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/508,307

(22) PCT Filed: Sep. 10, 1998

(86) PCT No.: PCT/EP98/05790

§ 371 Date: Mar. 9, 2000

§ 102(e) Date: Mar. 9, 2000

(87) PCT Pub. No.: WO99/14202

PCT Pub. Date: Mar. 25, 1999

(30) Foreign Application Priority Data

Sep. 12, 1997 (GB) .................................................. 9719411

(51) Int. Cl.$^7$ ................................................. C07D 239/00

(52) U.S. Cl. ........................................... 514/259; 544/278

(58) Field of Search .............................. 544/278; 514/259

(56) References Cited

FOREIGN PATENT DOCUMENTS

WO 97/02262 * 1/1997 (WO) .

* cited by examiner

*Primary Examiner*—Mukund J. Shah
*Assistant Examiner*—Hong Liu
(74) *Attorney, Agent, or Firm*—William A. Teoli, Jr.

(57) ABSTRACT

Novel pyrimidin-4-one and pyrimidin-4-thione derivatives of formula I

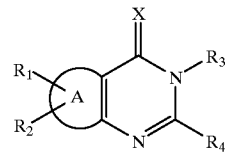

wherein

A is phenyl, thienyl (including all 3 isomers), thiazolyl, pyridyl or pyridazinyl;

X is oxygen or sulfur;

$R_1$ is hydrogen, halogen or trimethylsilyl, $R_2$ is hydrogen, halogen or trimethylsilyl; at least one of $R_1$ and $R_2$ is not hydrogen;

$R_3$ is $C_1$–$C_8$alkyl, $C_1$–$C_8$alkenyl, $C_1$–$C_8$alkinyl which are unsubstituted or mono to tri-substituted by $C_3$–$C_6$cycloalkyl, halogen, $C_1$–$C_6$alkoxy or $C_1$–$C_6$haloalkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_6$alkoxy; N—$C_1$–$C_6$alkyl; or N=CH$C_1$–$C_6$alkyl;

$R_4$ is $C_1$–$C_8$alkyl, $C_1$–$C_8$alkeanyl, $C_1$–$C_8$alkinyl which are unsubstituted or mono to tri-substituted by $C_3$–$C_6$cycloalkyl, halogen, cyano, $C_1$–$C_6$alkoxy or $C_1$–$C_6$haloalkoxy; $C_1$–$C_4$alkoxy-$C_1$–$C_4$alkoxy; $C_1$–$C_4$alkoxy-$C_1$–$C_4$alkylthio; nitro; —CO—$C_1$–$C_6$alkyl; $C_3$–$C_6$cycloalkyl; or phenyl, which is unsubstituted or mono to tri-substituted by halogen, $C_1$–$C_6$alkyl, $C_1$–$C_6$haloalkyl, $C_1$–$C_6$alkoxy, $C_1$–$C_6$haloalkoxy, cyano, nitro, amino, mono-$C_1$–$C_6$alkylamino, di-$C_1$–$C_6$alkyl-amino, $C_1$–$C_6$alkylthio, phenyl or phenoxy and in which the phenyl part is unsubstituted or mono to tri-substituted by halogen, $C_1$–$C_6$alkyl, $C_1$–$C_6$haloalkyl, $C_1$–$C_6$alkoxy or $C_1$–$C_6$haloalkoxy. The novel compounds have plant-protective properties and are suitable for protecting plants against infestation by phytopathogenic microorganisms, in particular fungi.

11 Claims, No Drawings

PYRIMIDIN-4-ONE AND PYRIMIDIN-4-THIONE AS FUNGICIDE

The present invention relates to novel pyrimidin-4-one and pyrimidin-4-thione derivatives of formula I, which have pesticidal activity, in particular fungicidal activity,

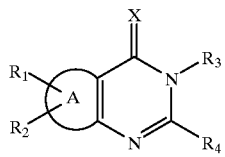

(I)

wherein
- A is phenyl, thienyl (including all 3 isomers), thiazolyl, pyridyl or pyridazinyl;
- X is oxygen or sulfur;
- $R_1$ is hydrogen, halogen or trimethylsilyl;
- $R_2$ is hydrogen, halogen or trimethylsilyl; at least one of $R_1$ and $R_2$ is not hydrogen;
- $R_3$ is $C_1$–$C_8$alkyl, $C_1$–$C_8$alkenyl, $C_1$–$C_8$alkinyl which are unsubstituted or mono to tri-substituted by $C_3$–$C_6$cycloalkyl, halogen, $C_1$–$C_6$alkoxy or $C_1$–$C_6$haloalkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_6$alkoxy; N—$C_1$–$C_6$alkyl; or N=CH$C_1$–$C_6$alkyl;
- $R_4$ is $C_1$–$C_8$alkyl, $C_1$–$C_8$alkenyl, $C_1$–$C_8$alkinyl which are unsubstituted or mono to tri-substituted by $C_3$–$C_6$cycloalkyl, halogen, cyano, $C_1$–$C_6$alkoxy or $C_1$–$C_6$haloalkoxy; $C_1$–$C_4$alkoxy-$C_1$–$C_4$alkoxy; $C_1$–$C_4$alkoxy-$C_1$–$C_4$alkylthio; nitro; —CO—$C_1$–$C_6$alkyl; $C_3$–$C_6$cycloalkyl; or phenyl, which is unsubstituted or mono to tri-substituted by halogen, $C_1$–$C_6$alkyl, $C_1$–$C_6$haloalkyl, $C_1$–$C_6$alkoxy, $C_1$–$C_6$haloalkoxy, cyano, nitro, amino, mono-$C_1$–$C_6$alkylamino, di-$C_1$–$C_6$alkyl-amino, $C_1$–$C_6$alkylthio, phenyl or phenoxy and in which the phenyl part is unsubstituted or mono to tri-substituted by halogen, $C_1$–$C_6$alkyl, $C_1$–$C_6$haloalkyl, $C_1$–$C_6$alkoxy or $C_1$–$C_6$haloalkoxy.

The invention also relates to the preparation of these compounds, to agrochemical compositions comprising as active ingredient at least one of these compounds, as well as to the use of the active ingredients or compositions for pest control, in particular as fungicides, in agriculture and horticulture.

The compounds I and, optionally, their tautomers may be obtained in the form of their salts. Because the compounds I have at least one basic center they can, for example, form acid addition salts. Said acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methanesulfonic acid or p-toluenesulfonic acid.

Together with at least one acidic group, the compounds of formula I can also form salts with bases. Suitable salts with bases are, for example, metal salts, typically alkali metal salts or alkaline earth metal salts, e.g. sodium salts, potassium salts or magnesium salts, or salts with ammonia or an organic amine, e.g. morpholine, piperidine, pyrrolidine, a mono-, di- or trialkylamine, typically ethylamine, diethylamine, triethylamine or dimethylpropylamine, or a mono-, di- or trihydroxyalkylamine, typically mono-, di- or triethanolamine. Where appropriate, the formation of corresponding internal salts is also possible. Within the scope of this invention, agrochemical acceptable salts are preferred.

Where asymmetrical carbon atoms are present in the compounds of formula I, these compounds are in optically active form. Owing to the presence of double bonds, the compounds can be obtained in the [E] and/or [Z] form. Atropisomerism can also occur. The invention relates to the pure isomers, such as enantiomers and diastereomers, as well as to all possible mixtures of isomers, e.g. mixtures of diastereomers, racemates or mixtures of racemates.

The general terms used hereinabove and hereinbelow have the following meanings, unless otherwise defined:

Alkyl groups on their own or as structural element of other groups such as alkoxy are, in accordance with the number of carbon atoms, straight-chain or branched and will typically be methyl, ethyl, n-propyl, isopropyl, n-butyl, sec-butyl, isobutyl, tert-butyl, n-amyl, tert-amyl, 1-hexyl, 3-hexyl, 1-heptyl or 1-octyl.

Alkenyl will be understood as meaning straight-chain or branched alkenyl such as allyl, methallyl, 1-methylvinyl, but-2-en-1-yl, 1-pentenyl, 1-hexenyl, 1-heptenyl or 1-octenyl. Preferred alkenyl radicals contain 3 to 4 carbon atoms in the chain.

Alkynyl can likewise, in accordance with the number of carbon atoms, be straight-chain or branched and is typically propargyl, but-1-yn-1-yl, but-1-yn-3-yl, 1-pentinyl, 1-hexinyl, 1-heptinyl or 1-octinyl. The preferred meaning is propargyl.

Halogen and halo substituents will be understood generally as meaning fluorine, chlorine, bromine or iodine. Fluorine, chlorine or bromine are preferred meanings.

Haloalkyl can contain identical or different halogen atoms, typically fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 3,3,3-trifluoropropyl.

Cycloalkyl is, depending on the ring size, cyclopropyl, cyclobutyl, cyclopentyl, cyclohexyl, cycloheptyl or cycooctyl.

Preferred compounds are those of formula I, wherein

A is thienyl, including all 3 isomers (subgroup A).

Within the scope of said subgroup A, those compounds of formula I are preferred wherein

- $R_1$ is hydrogen, fluorine, chlorine, bromine or iodine;
- $R_2$ is hydrogen, fluorine, chlorine, bromine or iodine; at least one of $R_1$ and $R_2$ is not hydrogen;
- $R_3$ is $C_1$–$C_6$alkyl, $C_2$–$C_6$alkenyl, $C_2$–$C_6$alkinyl which are unsubstituted or mono to tri-substitute by $C_3$–$C_6$cycloalkyl, halogen or $C_1$–$C_4$alkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_4$alkoxy; N—$C_1$–$C_6$alkyl; or N=CH$C_1$–$C_6$alkyl;
- $R_4$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkyoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine, bromine, $C_1$–$C_4$alkyl, $C_1$–$C_4$haloalkyl, $C_1$–$C_4$alkoxy or $C_1$–$C_4$haloalkoxy (subgroup B).

A special group within the scope of subgroup B is that of the compounds of formula I, wherein $R_3$ is $C_1$–$C_6$alkyl, $C_2$–$C_6$alkenyl, $C_2$–$C_6$alkinyl which are unsubstituted or mono to tri-substituted by $C_3$–$C_4$cycloalkyl, fluorine, chlorine, bromine or $C_1$–$C_4$alkoxy; O—$C_1$–$C_6$alkyl; O—$C_2$–$C_6$alkenyl; O—$C_2$–$C_6$alkynyl; N—$C_1$–$C_6$alkyl; or N=CH$C_1$–$C_6$alkyl;

$R_4$ is $C_1$–$C_6$alkyl, $C_2$–$C_6$alkenyl, $C_2$–$C_6$alkinyl which are unsubstituted or mono to tri-substituted by $C_3$–$C_4$cycloalkyl, fluorine, chlorine, bromine or $C_1$–$C_4$alkoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine or bromine (subgroup C).

A preferred group within the scope of subgroup C is that of the compounds of the formula I, wherein A is thienyl[2.3-d], X is oxygen, $R_1$ is hydrogen, chlorine or bromine;

$R_2$ is hydrogen, chlorine or bromine; at least one of $R_1$ and $R_2$ is not hydrogen;

$R_3$ is $C_3$–$C_5$alkyl or O—$C_1$–$C_4$alkyl;

$R_4$ is $C_2$–$C_5$alkyl or phenyl which is unsubstituted or mono to tri-substituted by fluorine, chlorine, bromine, $C_1$–$C_4$alkyl or phenoxy and in which the phenoxy is unsubstituted or mono to tri-substituted by fluorine, chlorine or bromine (subgroup D1).

Another preferred group within the scope of subgroup C is that of compounds of the formula I, wherein A is thienyl[2.3-d], X is sulfur, $R_1$ is hydrogen, chlorine or bromine;

$R_2$ is hydrogen, chlorine or bromine; at least one of $R_1$ and $R_2$ is not hydrogen;

$R_3$ is $C_3$–$C_5$alkyl or O—$C_1$–$C_4$alkyl;

$R_4$ is $C_2$–$C_5$alkyl or phenyl which is unsubstituted or mono to tri-substituted by fluorine, chlorine, bromine, $C_1$–$C_4$alkyl or phenoxy and in which the phenoxy is unsubstituted or mono to tri-substituted by fluorine, chlorine or bromine (subgroup D2).

Another preferred group within the scope of subgroup C is that of compounds of the formula I, wherein A is thienyl[3.2-d], X is oxygen, $R_1$ is hydrogen, chlorine or bromine;

$R_2$ is hydrogen, chlorine or bromine; at least one of $R_1$ and $R_2$ is not hydrogen;

$R_3$ is $C_3$–$C_5$alkyl or O—$C_1$–$C_4$alkyl;

$R_4$ is $C_2$–$C_5$alkyl or phenyl which is unsubstituted or mono to tri-substituted by fluorine, chlorine, bromine, $C_1$–$C_4$alkyl or phenoxy and in which the phenoxy is unsubstituted or mono to tri-substituted by fluorine, chlorine or bromine (subgroup E).

Another preferred group of compounds are those of formula I, wherein

A is pyridyl (subgroup F).

Within the scope of said group F, those compounds of formula I are preferred wherein X is oxygen;

$R_1$ is hydrogen, fluorine, chlorine, bromine or iodine;

$R_2$ is hydrogen, fluorine, chlorine, bromine or iodine; at least one of $R_1$ and $R_2$ is not hydrogen;

$R_3$ is $C_1$–$C_6$alkyl, $C_2$–$C_6$alkenyl, $C_2$–$C_6$alkinyl which are unsubstituted or mono to ri-substitute by $C_3$–$C_6$cycloalkyl, halogen or $C_1$–$C_4$alkoxy; O—$C_1$–$C_6$alkyl, O—$C_2$–$C_6$alkenyl, O—$C_2$–$C_6$alkynyl which are unsubstituted or mono to tri-substituted by $C_3$–$C_6$cycloalkyl, halogen or $C_1$–$C_4$alkoxy;

$R_4$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine, bromine, $C_1$–$C_4$alkyl, $C_1$–$C_4$haloalkyl, $C_1$–$C_4$alkoxy or $C_1$–$C_4$haloalkoxy (subgroup G).

Other preferred group of compounds are those of formula I, wherein

A is phenyl (subgroup H).

Within the scope of said group H, those compounds of formula I are preferred wherein X is oxygen;

$R_1$ is hydrogen, fluorine, chlorine, bromine or iodine;

$R_2$ is hydrogen, fluorine, chlorine, bromine or iodine; at least one of $R_1$ and $R_2$ is not hydrogen;

$R_3$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_4$alkoxy; N—$C_1$–$C_6$alkyl; or N=CH$C_1$–$C_6$alkyl;

$R_4$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine, bromine, $C_1$–$C_4$alkyl, $C_1$–$C_4$haloalkyl, $C_1$–$C_4$alkoxy or $C_1$–$C_4$haloalkoxy (subgroup J1).

Another preferred group within the scope of subgroup H is that of compounds of the formula I, wherein X is sulfur;

$R_1$ is hydrogen, fluorine, chlorine or bromine;

$R_2$ is hydrogen, fluorine, chlorine or bromine; at least one of $R_1$ and $R_2$ is not hydrogen;

$R_3$ is $C_1$–$C_6$alkyl, $C_2$–$C_6$alkenyl, $C_2$–$C_6$alkinyl which are unsubstituted or mono to tri-substitute by $C_3$–$C_6$cycloalkyl, halogen or $C_1$–$C_4$alkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_4$alkoxy;

$R_4$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine, bromine, $C_1$–$C_4$alkyl, $C_1$–$C_4$haloalkyl, $C_1$–$C_4$alkoxy or $C_1$–$C_4$haloalkoxy (subgroup J2).

Other preferred groups of compounds are those of formula I, wherein

A is thiazolyl (subgroup K).

Within the scope of said group K, those compounds of formula I are preferred wherein X is oxygen;

$R_1$ is hydrogen, fluorine, chlorine, bromine or iodine;

$R_2$ is hydrogen, fluorine, chlorine, bromine or iodine; at least one of $R_1$ and $R_2$ is not hydrogen;

$R_3$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_4$alkoxy;

$R_4$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine, bromine, $C_1$–$C_4$alkyl, $C_1$–$C_4$haloalkyl, $C_1$–$C_4$alkoxy or $C_1$–$C_4$haloalkoxy (subgroup L).

Another preferred group of compounds are those of formula I, wherein

A is pyridazinyl (subgroup M).

Within the scope of said group M, those compounds of formula I are preferred wherein X is oxygen;

$R_1$ is hydrogen, fluorine, chlorine, bromine or iodine;

$R_2$ is hydrogen, fluorine, chlorine, bromine or iodine; at least one of $R_1$ and $R_2$ is not hydrogen;

$R_3$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_4$alkoxy;

$R_4$ is $C_1$–$C_6$alkyl, $C_2$–$C_6$alkenyl, $C_2$–$C_6$alkinyl which are unsubstituted or mono to tri-substituted by $C_3$–$C_6$cycloalkyl, halogen or $C_1$–$C_4$alkoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine, bromine, $C_1$–$C_4$alkyl, $C_1$–$C_4$haloalkyl, $C_1$–$C_4$alkoxy or $C_1$–$C_4$haloalkoxy (subgroup N).

The compounds of formula I can be prepared as follows:

Scheme 1

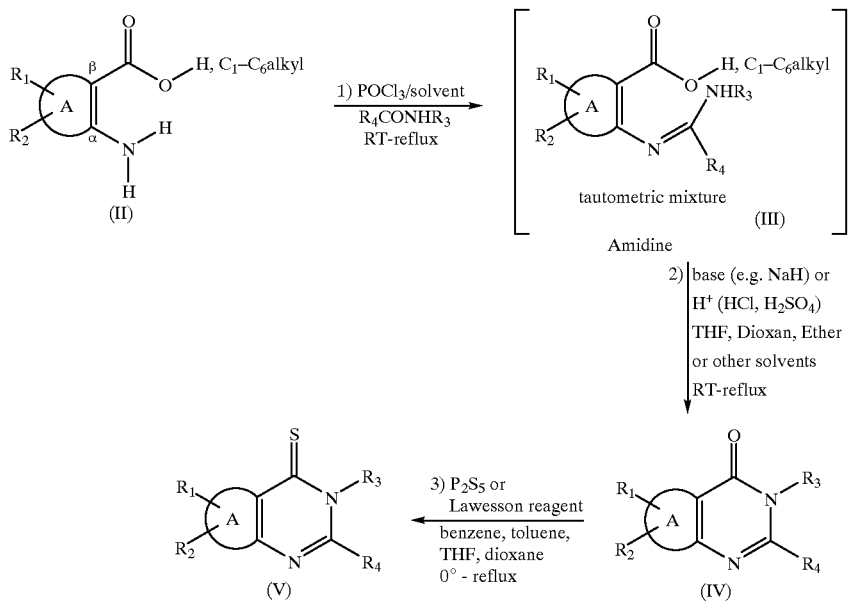

The compounds of formula I are preferably prepared starting from α-amino-β-carboalkoxyheterocycles or α-amino-β-carbocyclic acid heterocycles, some of which, where Het=thienyl, are commercially available (2 isomers). The methyl thiophene-2-amino-3-carboxylate can be prepared, for example, in accordance with Acta Pharm. Suecica 1968, Vol. 5, p.563, according to S. Gronowitz et al. Other heterocycles can be prepared according to instructions in the literature. The synthesis of, for example, ethyl 5-aminothiazole-4-carboxylate and ethyl 5-amino-2-methylthiazole4-carboxylate is described by Golankiewicz et al. in Tetrahedron 1985, 41, 5989. The reaction of the α-amino-β-carboalkoxyheterocycles or α-amino-β-carbocyclic acid heterocycles with amides ($R_4CONHR_3$) (step 1 in scheme 1) is conveniently carried out in the presence of $POCl_3$, $SOCl_2$ or $SO_2Cl_2$, in solvents, such as ClCH$_2$CH$_2$Cl, CHCl$_3$, CH$_2$Cl$_2$, benzene, toluene, hexane, cyclohexane or others in the temperature range from RT to retlux temperature. The resulting amidines (III) either cyclise spontaneously to the pyrimidin-4-ones or were converted into the cyclised products by treatment with bases such as t-Butyl-O—K, NaH, KH, n-BuLi, NaOH, Na$_2$CO$_3$ or others in solvents such as THF, dioxane, hexane, toluene, DMSO, DMF, dimethylacetamid or others at temperatures between 20° C. and reflux-temperature.

The replacement of the 4-one group with sulfur to the 4-thione group (step 3 in scheme 1) is carried out by reaction with P$_2$S$_5$ or Lawesson-reagent in tetrahydrofurane, dioxane or toluene as solvent in the temperature range of RT to reflux temperature.

The above synthesis route is the first disclosure of how to prepare 3H-thieno[2.3-d]-pyrimidin-4-one derivatives within the structural pattern of formula I herein.

Methods for the preparation of compounds of the general formula I wherein R$_1$=R$_2$=hydrogen are described in Chemical Scripta 1981, 18, 135, Synthesis 1977, 180, Chem.Pharm.Bull. 1989, 37,2122 and DE-OS-2411273.

The invention also relates to the intermediates of the formula III, IV and V, and especially to those wherein A represents thienyl[2.3-d].

The introduction of further substituents into the 5-ring of the thienopyrimidin-4-ones may also conveniently be carried out using metallorganic methodology. Thieno[3.2-d]-pyrimidin-4-ones and thieno[2.3-d]pyrimidin-4ones, for example, can be deprotonised selectively in 6-position. Particularly suitable bases for this purpose are lithium diisopropylamide (LDA), lithium cyclohexylisopropylamide (LICA) or secondary butyl lithium/TMEDA. A great number of the radicals R$_1$ or R$_2$ indicated above can be introduced by reacting the resulting anions with electrophiles (step 1 in scheme 2), typically Br$_2$, NBS, F$_2$, ICl, Cl$_2$, F$^+$ reagents, trimethylsilyl chloride.

Scheme 2
Synthesis of special heterocycles

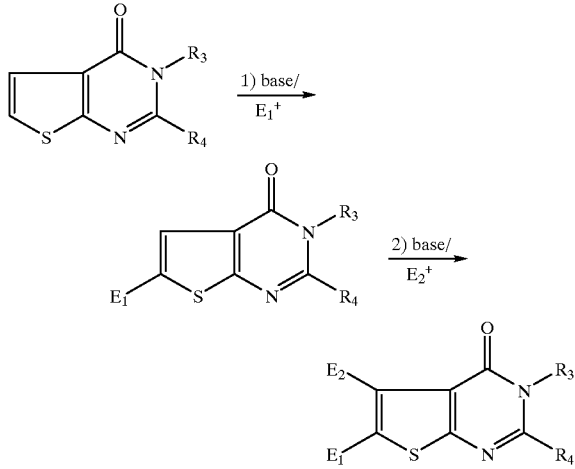

E$^+_{1,2}$ = NBS (N-Bromsuccinimide), NCS (N- Chlorsuccinmide), I$_2$,
Cl$_2$, Br$_2$, FCl, F$^+$ reagents, TMS and similar Si reagents.

The following compounds can likewise be prepared in general accordance with the methods described in scheme 2:

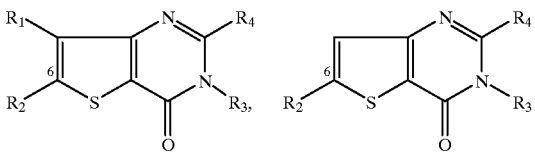

Scheme 3: synthesis of especial thienopypirimidin-4-ones (special methods for the introduction of halogen into thiopene ring)

a) Thieno[2.3-d]pyrimidin-4-ones:

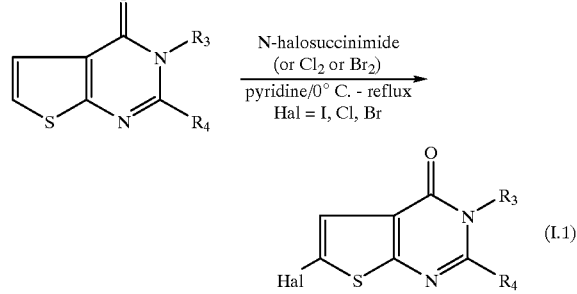

1–3 molar equivalents of N-bromosuccinimide or N-chlorosuccinimide (or Cl$_2$ gas or Br$_2$) are used for halogenation. The solvent used is, for example, pyridine in the temperature range from 0° C. to reflux. The reaction time is 1 to 24 hours.

a2) "Pure" chlorinating method:

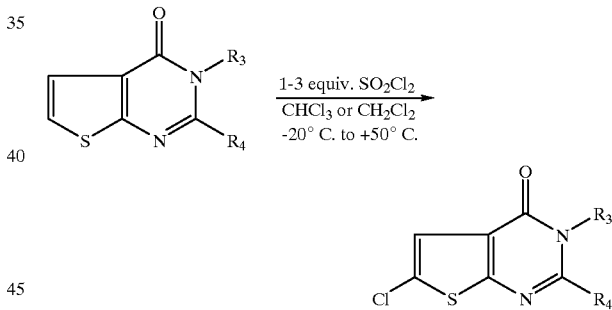

The described reactions are carried out in per se known manner, e.g. in the presence or absence of a suitable solvent or diluent or of a mixture thereof, if appropriate with cooling, at room temperature or with heating, e.g. in the temperature range from about –20° C. to the boiling temperature of the reaction medium, preferably in the range from about –20° C. to about +150° C. and, if required, in a closed vessel, under pressure, in an inert gas atmosphere and/or under anhydrous conditions.

Illustrative examples of such solvents or diluents are: aromatic, aliphatic and alicyclic hydrocarbons and halogenated hydrocarbons, typically benzene, toluene, xylene, chlorobenzene, bromobenzene, petroleum ether, hexane, cyclohexane, dichloromethane, trichloromethane, dichloroethane or trichloroethane; ethers, typically diethyl ether, tert-butylmethyl ether, tetrahydrofuran or dioxane; ketones, typically acetone or methyl ethyl ketone; alcohols, typically methanol, ethanol, propanol, butanol, ethylene glycol or glycerol; esters, typically ethyl acetate or butyl acetate; amides, typically N,N-dimethylformamide, N,N- dimethylacetamide, N-methylpyrrolidone or hexamethylphosphoric acid triamide; nitrites, typically acetonitrile; and sulfoxides, typically dimethylsulfoxide. Bases used in excess, such as triethylamine, pyridine, N-methylmorpholine or N,N-diethylaniline, can also be used as solvents or diluents.

Suitable bases are, for example, alkali metal hydroxide or alkaline earth metal hydroxide, alkali metal hydride or alkaline earth metal hydride, alkali metal amide or alkaline earth metal amide, alkali metal alkanolate or alkaline earth metal alkanolate, alkali metal carbonate or alkaline earth metal carbonate, alkali metal dialkylamide or alkaline earth metal dialkylamide, or alkali metal alkylsilylamide or alkaline earth metal alkylsilylamide, alkylamines, alkylenediamines, optionally N-alkylated, optionally unsaturated cycloalkylamines, basic heterocycles, ammonium hydroxides and carbocyclic amines. Examples meriting mention are sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyltrimethylammonium hydroxide, and 1,8diazabicyclo[5.4.0]undec-5-ene (DBU).

The compounds of the formula I can also be prepared as follows absence of a suitable solvent or diluent, if required in the presence of an acid catalyst at room temperature or with heating, e.g. in the temperature range fromn about 20 to 200° C. Illustrative examples of solvents or diluents are ethers like tert.butylmethylether, tetrahydrofurane, dimethylether, amides like N,N-dimethylformamide or N-methylpyrrolidone; sulfoxides, typically dimethylsulfoxid and alcohols like methanol, ethanol, propanol, butanol, ethylene glycol or glycerol. As catalyst can be used hydrogen halides, methanesulfonic acid, triflouromethyl aceticacid, p-toluenesulfonic acid and others in the absence of water. Commonly used bases are sodium hydroxid, potassium hydroxid, sodium hydrogencarbonate, sodium carbonate, sodium hydride, potassium hydride, potassium carbonate and others.

Especially for the thienopyrimidinone, scheme 5 describes the reaction of the aminothiophene-carboxylic-acid amide VIa with the orthoester XIII in the presence or absence of a solvent, if required in the presence of an acid catalyst in the temperature range from 20 to 200° C. The resulting intermediate VIIa is then halogenated in the presence of a solvent at temperatures from 20° C. to reflux. The halogenated intermediate VIIIa is than cyclised in the presence of a base, in the presence or absence of a suitable solvent at temperatures from 20° C. to reflux. Halogenation reagents are typically N-Bromsuccinimide, N-Chlorsuccinimide, N-iodsuccinimide, Chlorgas, $Br_2$, thionylchloride and others. Preferably solvents used for the

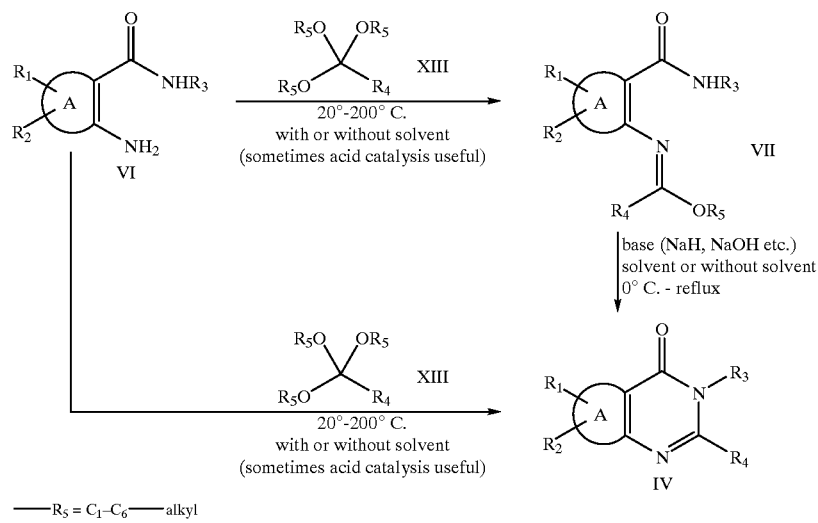

Scheme 4

The amino carboxylic acidamide of formula VI reacts with the orthoester of formula XIII in the presence or halogenation are tert.-butylmethylether, tetrahydrofurane, chloroform, methylenechloride, pyridine and quinoline.

Scheme 5

(Thienopyrimidinones)

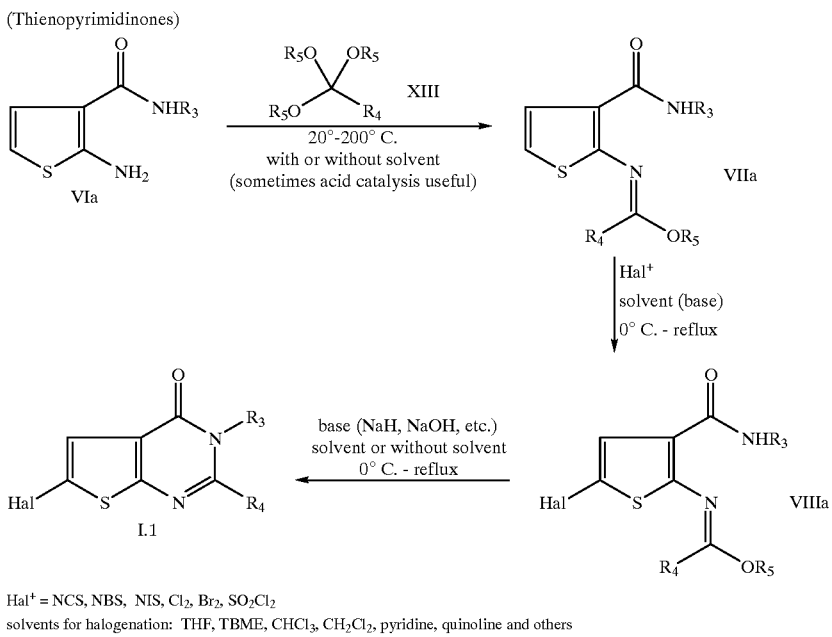

Hal+ = NCS, NBS, NIS, $Cl_2$, $Br_2$, $SO_2Cl_2$
solvents for halogenation: THF, TBME, $CHCl_3$, $CH_2Cl_2$, pyridine, quinoline and others Another alternative is described in scheme 6, in which the amino-carboalkoxy-thiophene of formula IIa reacts with the orthoester XIII to the intermediate IXa, than the compound IXa is transformed to the amidine IIIa and cyclised to the thienopyrimidinone X. The halogenation of X to obtain I.1 is as described in Scheme 3.

Scheme 6

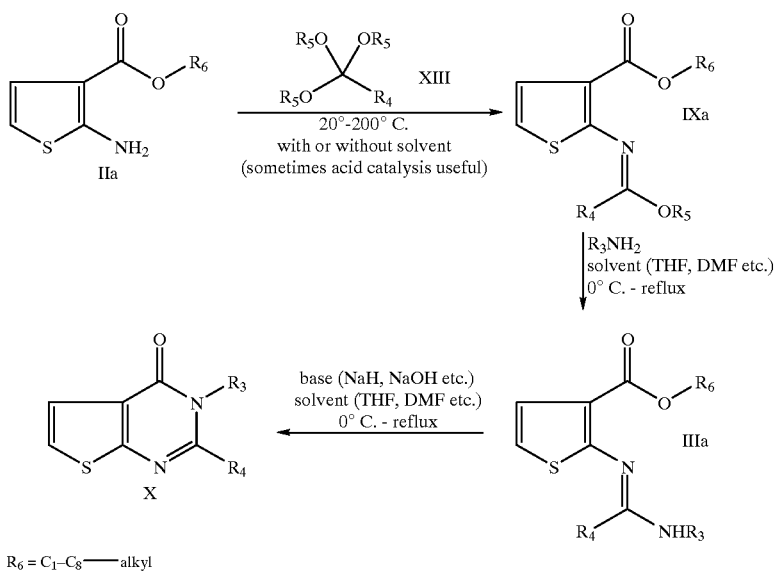

$R_6 = C_1-C_8$ — alkyl

The reaction conditions from IIa to IXa is as described in the schemes 4 or 5, as well as the cyclisation from IIIa to X is as described above. The reaction from IXa to IIIa requires as solvent for example tetrahydrofurane, N,N-dimethylformamide or others at a temperature range from 0° C. to reflux.

The scheme 7 describes the reaction of the compound IIa with the orthoester XIII to obtain the intermediate IXa, which is converted to the intermediate IIIa and than halogenated to the thiophene XIa. Cyclisation of XIa gives the compound I.1.

Scheme 7

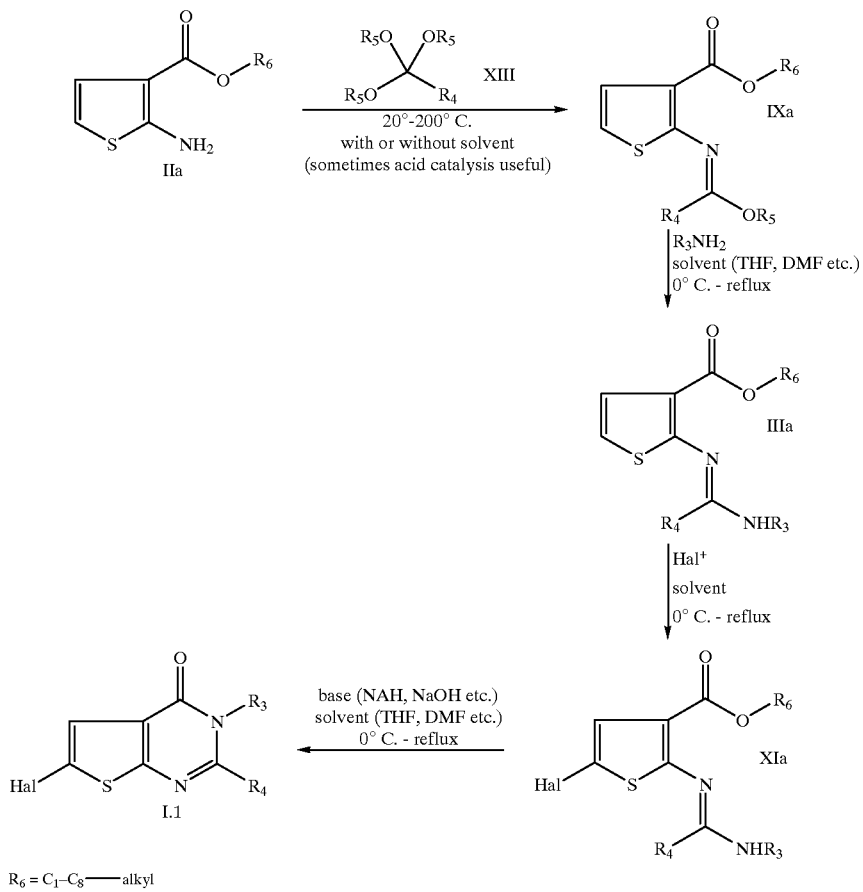

The reactions conditions described in process 4 are as described analogously in the schemes 4, 5 or 6.

Scheme 8 describes the alternative route comprising the reaction of the compound IIa with the orthoester XIII to the intermediate IXa, which is halogenated to the intermediate XIIa and than converted to the thiophene XIa. Cyclisation of XIa gives the end product I.1. The reactions conditions are as described in the schemes 4, 5, 6 and 7.

Scheme 8

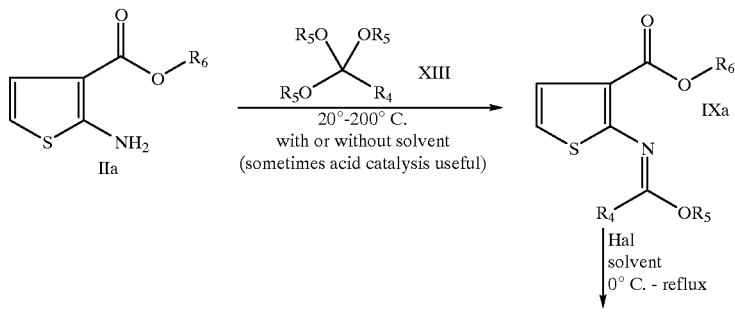

-continued

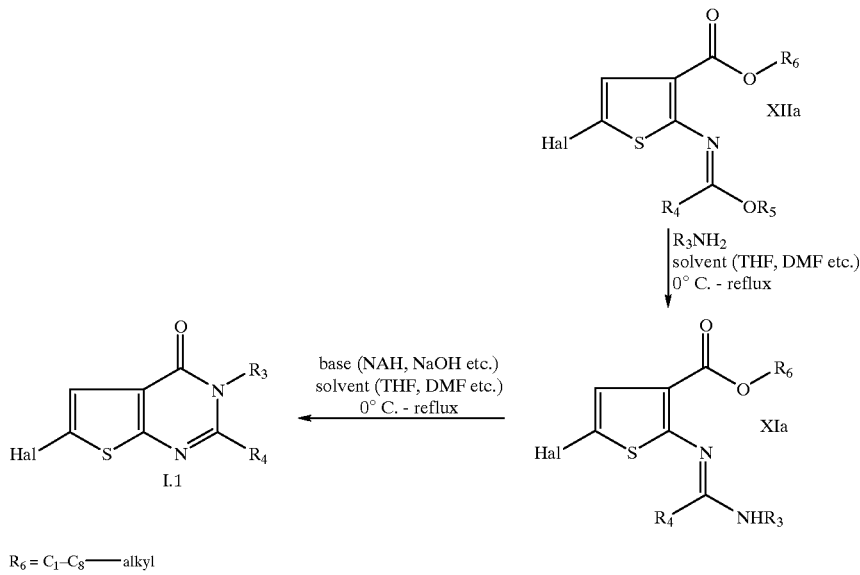

$R_6 = C_1-C_8-\text{alkyl}$

Quinazolinone derivatives having fungicidal properties are known from WO-94/26722 or EP-A-276825 and thienopyrimidinenes are known from WO-97/02262.

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. Botrytis, Pyricularia, Helminthosporium, Fusarium, Septoria, Cercospora and Altemaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Furthermore, the novel compounds of formula I are effective against phytopathogenic bacteria and viruses (e.g. against Xanthomonas spp, Pseudomonas spp, *Erwinia amylovora* as well as against the tobacco mosaic virus).

Within the scope of this invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines, hops, bananas and natural rubber plants, as well as ornamentals.

The compounds of formula I are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazoie, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-aminopyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129 or 2-[α{[(α-methyl-3-trifluoromethyl-benzyl)imino]-oxy}-o-tolyl]-glyoxylic acid-methylester-O-methyloxime; dithiocarbamates such as ferbam, mancozeb, maneb, metiram, propineb, thiram, zineb or ziram; N-halomethylthiodicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine or validamycin.

Preferred compound for mixing with the above-mentioned mixing components is compound no. 3.30.

Another preferred compound for mixing with the above-mentioned mixing components is compound no. 3.31.

Another preferred compound for mixing with the above-mentioned mixing components is compound no. 3.58.

Another preferred compound for mixing with the above-mentioned mixing components is compound no. 3.59.

Suitable carriers and adjuvants can be solid or liquid and are substances useful in formulation technology, e.g. natural or regenerated mineral substances, solvents, dispersants, wetting agents, tackifiers, thickeners, binders or fertilizers.

A preferred method of applylng a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The compounds of formula I are used in unmodified form or, preferably, together with the adjuvants conventionally employed in the art of formulation. To this end they are convenientty formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

The following non-limitative Examples illustrate the above-described invention in more detail. Temperatures are given in degrees Celsius. The following abbreviations are used: Et=ethyl; i-propyl=isopropyl; Me=methyl; m.p.=melting point. "NMR" means nuclear magnetic resonance spectrum. MS=mass spectrum. "%" is percent by weight, unless corresponding concentrations are indicated in other units.

PREPARATION EXAMPLES

Example P-1

2-(1-n-butyl-1-methoxymethyleneamino)thiophene-3-carboxylic-acid propylamide

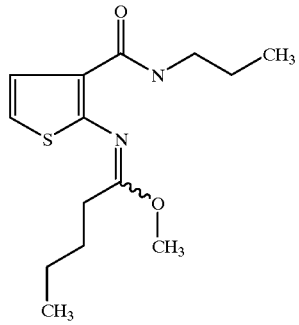

In a destillation apparatus, a mixture of 1.84 g of 2-aminothiophene-3-carboxylic-acid propylamide and 2.43 g of trimethyl orthovalerate is heated for 2 hours at 130° C. Methanol, which arises during the reaction is directly distilled out of the reaction flask. After cooling, the crude product is purified by column chromatography (eluant:hexane/ethylacetate=1:2). Yield:1.9 g pure 2-(1-n-butyl-1-methoxymethyleneamino)thiophene-3-carboxylic-acid propylamide; m.p. 68–70° C.

Example P-2

5-Chloro-2-(1-n-butyl-1-methoxymethyleneamino)thiophene-3-carboxylic-acid propylamide

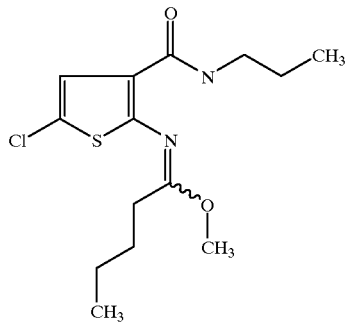

In a sulfonation flask 0.85 g 2-(1-n-butyl-1-methoxymethyleneamino)thiophene-3-carboxylic-acid propylamide are added with stirring to 10 ml absolute pyridine. The internal temperature is then raised to 60° C. and 0.5 g of N-chlorosuccinimide (NCS) are added in two portions. After stirring for 1 hour at 60° C., the pyridine is removed in a water jet vacuum. The residue is taken up in ethylacetate and the organic phase is washed twice with water. After drylng of the organic phase, the solvent is removed in a water jet vacuum and the raw material purified by column chromatography over silica gel (eluant:hexane/ethylacetate=3:1). Yield: 0.6 g 5-Chloro-2-(1-n-butyl-1-methoxymethyleneamino)thiophene-3-carboxylic-acid propylamide in the form of brownish crystalls; m.p. 110–112° C.

Example P-3

2-n-Butyl-3-n-propyl-3H-thieno[2,3-d]pyrimidin-4-one

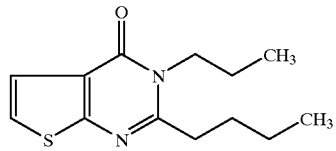

In a sulfonation flask, 0.85 g of 2-(1-n-butyl-1-methoxymethyleneamino)-thiophene-3-carboxylicacid propylamide is dissolved in 20 ml of absolute THF and 0.15 g of a ca. 55% NaH dispersion is added in small portions. The mixture is stirred for 15 minutes at room temperature and 1 hour at reflux temperature. Then the solvent is removed in a water jet vacuum and the residue taken up in ethylacetate. The organic phase is washed twice with water and after drying of the organic phase with sodium sulfate, the solvent is removed in a water jet vacuum. The resulting crude product (yleld: 0.8 g of 2-n-butyl-3-n-propyl-3H-thieno[2,3-d]-pyrimidine-4-one in the form of a brown liquid) can be used without further purification for the halogenation step.

Example P-4

2-n-butyl-6-chloro-3-n-propyl-3H-thieno[2,3-d]pyrimidine-4-one

[cmpd. 3.31]

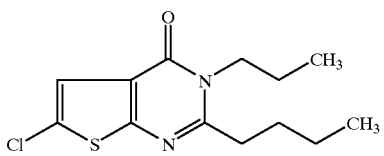

In a sulfonation flask, 0.36 g of 5–Chloro-2-(1-n-butyl-1-methoxymethyleneamino)thiophene-3-carboxylic-acid propylamide is dissolved in 20 ml of absolute THF and 0.085 g of a ca. 55% NaH dispersion is added in one portion. The mixture is stirred for 15 minutes at room temperature and 1 hour at reflux temperature. Then the solvent is removed in a water jet vacuum and the residue taken up in ethylacetate. The organic phase is washed twice with water and after drylng of the organic phase with sodium sulfate, the solvent is removed in a water jet vacuum. The resulting crude product is purified by column chromatography over silica gel (eluant:hexane/ethylacetate=5:1). Yield: 0.2 g 2-n-butyl-6-chloro-3-n-propyl-3H-thieno[2,3-d]pynimidin-4-one in the form of a slightly yellowish powder; m.p. 67–69° C.

Example P-3a 2-n-butyl-3-n-propyl-3H-thieno[2.3-d]pyrimidin-4-one

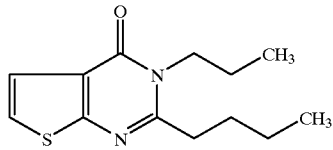

In a sulfonation flask, 11.0 g (70 mmol) of 2-amino-3-carbomethoxythiophen and 10.9 g (76 mmol) valeric acid propylamide are added to 60 ml 1,2-dichloroethane. Under stirring and at room temperature 7 ml of phosphoroxychloride is slowly added dropwise. After 3 hours at reflux temperature the mixture is poored into ice water and adjusted light alkali with sodium hydrogencarbonat. The resulting mixture is then extracted three times with methylenechloride and the separated organic phase dried over sodium sulfate. The solvent is then removed in a water-jet vacuum.

In a sulfonation flask, the crude product is added to 100 ml of absolute tetrahydrofurane and under stirring 4.36 g (0.1 mol) NaH in 50 ml abs. THF is carefully added. After stirring for 2 hours at reflux temperature, the solvent is removed in a water-jet vacuum and the residue is taken up in ethyl acetate/water. The water-phase is extracted with additionally ethyl acetate. The organic phase is dried over sodium sulfate and the solvent removed in a waterjet vacuum. The crude product is purified by column chromatography over silica gel (eluant:TBME/hexane=1:2). 12.0 g of 2-n-butyl-3-n-propyl-3H-thieno[2.3-d]pyrimidin-4-one are obtained in the form of a yellow powder having a melting point of 70–72° C.

Example P-4a 2-n-butyl-6-chloro-3-n-propyl-3H-thieno-[2.3-d]pyrimidin-4-one

[cmpd. no. 3.31]

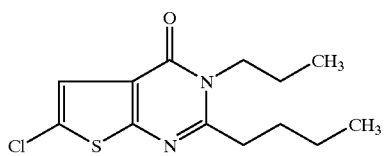

In a sulfonation flask, 2.0 g (8 mmol) of 2-n-butyl-3-propyl-3H-thieno[2.3-d]pyrimidin-4-one are added, with stirring, to 15 ml of absolute pyridine. The internal temperature is then raised to 80° C. and then 1.87 g (14 mmol) of N-chlorosuccinimide (NCS) are added in smallish portions. After stirring for 3 hours at 90° C. 1.0 g of NCS is added and the mixture is stirred another 3 hours at 90° C. The pyridine is removed in a water-jet vacuum and the crude product so obtained is purified by column chromatography over silica gel (eluant:n-hexane/tert.butylmethylether=3:1), giving 0.9 g of 2-n-butyl-6-chloro-3-propyl-3H-thieno-[2.3-d]pyrimidin-4-one in the form of a beige powder having a melting point of 67–69° C.

TABLE 1

A = Phenyl

| cmpd. No. | $R_1$ | $R_2$ | $R_3$ | $R_4$ | phys. data m.p. °C. |
|---|---|---|---|---|---|
| 1.1 | 6-Br | H | Me | Me | |
| 1.2 | 6-Cl | H | Me | Et | |
| 1.3 | 6-Br | H | Me | n-Propyl | |
| 1.4 | 6-Cl | H | Me | n-Propyl | |
| 1.5 | H | 7-Cl | Me | n-Propyl | |
| 1.6 | 6-Br | H | Me | n-Butyl | |
| 1.7 | 6-Cl | H | Me | n-Butyl | |
| 1.8 | H | 7-Cl | Me | n-Butyl | |
| 1.9 | 6-Br | H | Me | i-Butyl | |
| 1.10 | 6-Cl | H | Me | i-Butyl | |
| 1.11 | 6-Br | H | Me | n-Pentyl | |
| 1.12 | 6-Br | H | Me | cyclopropyl-CH$_2$ | |
| 1.13 | 6-Cl | H | Me | cyclopropyl-CH$_2$ | |
| 1.14 | 6-Br | H | Et | Me | |
| 1.15 | 6-Cl | H | Et | Et | |
| 1.16 | 6-Br | H | Et | n-Propyl | |
| 1.17 | 6-Cl | H | Et | n-Propyl | |
| 1.18 | H | 7-Cl | Et | n-Propyl | |
| 1.19 | 6-Br | H | Et | n-Butyl | |
| 1.20 | 6-Cl | H | Et | n-Butyl | |
| 1.21 | H | 7-Cl | Et | n-Butyl | |
| 1.22 | 6-Br | H | Et | i-Butyl | |
| 1.23 | 6-Cl | H | Et | i-Butyl | |
| 1.24 | 6-Br | H | Et | n-Pentyl | |
| 1.25 | 6-Br | H | Et | cyclopropyl-CH$_2$ | |
| 1.26 | 6-Cl | H | Et | cyclopropyl-CH$_2$ | |
| 1.27 | 6-Br | H | n-Propyl | Me | |
| 1.28 | 6-Cl | H | n-Propyl | Et | |
| 1.29 | 6-Br | H | n-Propyl | n-Propyl | |
| 1.30 | 6-Cl | H | n-Propyl | n-Propyl | |
| 1.31 | H | 7-Cl | n-Propyl | n-Propyl | |
| 1.32 | H | 7-I | n-Propyl | n-Propyl | |
| 1.33 | 6-Br | H | n-Propyl | cyclopropyl | |
| 1.34 | 6-Cl | H | n-Propyl | cyclopropyl | |
| 1.35 | H | 7-Cl | n-Propyl | cyclopropyl | |
| 1.36 | 6-Br | H | n-Propyl | n-Butyl | 130–135 |
| 1.37 | 6-Cl | H | n-Propyl | n-Butyl | |

TABLE 1-continued

A = Phenyl

| cmpd. No. | R₁ | R₂ | R₃ | R₄ | phys. data m.p. ° C. |
|---|---|---|---|---|---|
| 1.38 | H | 7-Cl | n-Propyl | n-Butyl | |
| 1.39 | H | 7-I | n-Propyl | n-Butyl | |
| 1.40 | 6-Br | H | n-Propyl | i-Butyl | |
| 1.41 | 6-Cl | H | n-Propyl | i-Butyl | |
| 1.42 | 6-Br | H | n-Propyl | cyclopropyl | |
| 1.43 | 6-Cl | H | n-Propyl | cyclopropyl | |
| 1.44 | H | 7-Cl | n-Propyl | cyclopropyl | |
| 1.45 | 6-Br | H | n-Propyl | cyclopropyl | |
| 1.46 | 6-Cl | H | n-Prpyl | 2-Me-cyclopropyl | |
| 1.47 | 6-Br | H | n-Propyl | Cyclobutyl | |
| 1.48 | 6-Br | H | n-Propyl | n-Pentyl | |
| 1.49 | 6-Cl | H | n-Propyl | n-Pentyl | |
| 1.50 | H | 7-Cl | n-Propyl | n-Pentyl | |
| 1.51 | 6-Br | H | n-Propyl | Cyclopentyl | |
| 1.52 | 6-Br | H | n-Propyl | n-Hexyl | |
| 1.53 | 6-Br | H | n-Propyl | Cyclohexyl | |
| 1.54 | 6-Br | H | n-Propyl | Phenyl | |
| 1.55 | 6-Br | H | n-Propyl | 4-Chloro-phenyl | |
| 1.56 | 6-Cl | H | n-Propyl | 4-Chloro-phenyl | |
| 1.57 | 6-Br | H | n-Propyl | 4-Phenoxy-phenyl | |
| 1.58 | 6-Br | H | n-Butyl | Me | |
| 1.59 | 6-Cl | H | n-Butyl | Et | |
| 1.60 | 6-Br | H | n-Butyl | n-Propyl | |
| 1.61 | 6-Cl | H | n-Butyl | n-Propyl | |
| 1.62 | H | 7-Cl | n-Butyl | n-Propyl | |
| 1.63 | H | 7-I | n-Butyl | n-Propyl | |
| 1.64 | 6-Br | H | n-Butyl | cyclopropyl | |
| 1.65 | 6-Cl | H | n-Butyl | cyclopropyl | |
| 1.66 | H | 7-Cl | n-Butyl | cyclopropyl | |
| 1.67 | 6-Br | H | n-Butyl | n-Butyl | |
| 1.68 | 6-Cl | H | n-Butyl | n-Butyl | |
| 1.69 | H | 7-Cl | n-Butyl | n-Butyl | |
| 1.70 | H | 7-I | n-Butyl | n-Butyl | |
| 1.71 | 6-Br | H | n-Butyl | i-Butyl | |
| 1.72 | 6-Cl | H | n-Butyl | i-Butyl | |
| 1.73 | 6-Br | H | n-Butyl | cyclopropyl | |
| 1.74 | 6-Cl | H | n-Butyl | cyclopropyl | |
| 1.75 | H | 7-Cl | n-Butyl | cyclopropyl | |
| 1.76 | 6-Br | H | n-Butyl | 2-Me-cyclopropyl | |
| 1.77 | 6-Cl | H | n-Butyl | 2-Me-cyclopropyl | |
| 1.78 | 6-Br | H | n-Butyl | Cyclobutyl | |
| 1.79 | 6-Br | H | n-Butyl | n-Pentyl | |
| 1.80 | 6-Cl | H | n-Butyl | n-Pentyl | |
| 1.81 | H | 7-Cl | n-Butyl | n-Pentyl | |
| 1.82 | 6-Br | H | n-Butyl | Cyclopentyl | |
| 1.83 | 6-Br | H | n-Butyl | n-Hexyl | |
| 1.84 | 6-Br | H | n-Butyl | Cyclohexyl | |
| 1.85 | 6-Br | H | n-Butyl | Phenyl | |
| 1.86 | 6-Br | H | n-Butyl | 4-Chloro-phenyl | |
| 1.87 | 6-Cl | H | n-Butyl | 4-Chloro-phenyl | |
| 1.88 | 6-Br | H | n-Butyl | 4-Phenoxy-phenyl | |
| 1.89 | 6-Br | H | i-Butyl | n-Propyl | |
| 1.90 | 6-Cl | H | i-Butyl | n-Propyl | |
| 1.91 | 6-Br | H | i-Butyl | n-Butyl | |
| 1.92 | 6-Cl | H | i-Butyl | n-Butyl | |
| 1.93 | 6-Br | H | cyclopropyl-CH₂ | n-Propyl | |
| 1.94 | 6-Cl | H | cyclopropyl-CH₂ | n-Propyl | |

TABLE 1-continued

A = Phenyl

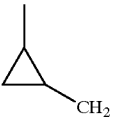

| cmpd. No. | R₁ | R₂ | R₃ | R₄ | phys. data m.p. °C. |
|---|---|---|---|---|---|
| 1.95 | 6-Br | H | 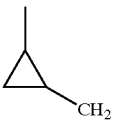 | n-Propyl | |
| 1.96 | 6-Br | H |  | n-Butyl | |
| 1.97 | 6-Br | H | n-Pentyl | Me | |
| 1.98 | 6-Cl | H | n-Pentyl | Et | |
| 1.99 | 6-Br | H | n-Pentyl | n-Propyl | |
| 1.100 | 6-Cl | H | n-Pentyl | n-Propyl | |
| 1.101 | H | 7-Cl | n-Pentyl | n-Propyl | |
| 1.102 | H | 7-I | n-Pentyl | n-Propyl | |
| 1.103 | 6-Br | H | n-Pentyl |  | |
| 1.104 | 6-Cl | H | n-Pentyl |  | |
| 1.105 | H | 7-Cl | n-Pentyl |  | |
| 1.106 | 6-Br | H | n-Pentyl | n-Butyl | |
| 1.107 | 6-Cl | H | n-Pentyl | n-Butyl | |
| 1.108 | H | 7-Cl | n-Pentyl | n-Butyl | |
| 1.109 | H | 7-I | n-Pentyl | n-Butyl | |
| 1.110 | 6-Br | H | n-Pentyl | i-Butyl | |
| 1.111 | 6-Cl | H | n-Pentyl | i-Butyl | |
| 1.112 | 6-Br | H | n-Pentyl |  | |
| 1.113 | 6-Cl | H | n-Pentyl |  | |
| 1.114 | H | 7-Cl | n-Pentyl |  | |
| 1.115 | 6-Br | H | n-Pentyl |  | |
| 1.116 | 6-Cl | H | n-Pentyl |  | |
| 1.117 | 6-Br | H | n-Pentyl | Cyclobutyl | |
| 1.118 | 6-Br | H | n-Pentyl | n-Pentyl | |
| 1.119 | 6-Cl | H | n-Pentyl | n-Pentyl | |
| 1.120 | H | 7-Cl | n-Pentyl | n-Pentyl | |
| 1.121 | 6-Br | H | n-Pentyl | Cyclopentyl | |
| 1.122 | 6-Br | H | n-Pentyl | n-Hexyl | |
| 1.123 | 6-Br | H | n-Pentyl | Cyclohexyl | |
| 1.124 | 6-Br | H | n-Pentyl | Phenyl | |
| 1.125 | 6-Br | H | n-Pentyl | 4-Chlorophenyl | |
| 1.126 | 6-Cl | H | n-Pentyl | 4-Chlorophenyl | |
| 1.127 | 6-Br | H | n-Pentyl | 4-Phenoxyphenyl | |
| 1.128 | 6-Br | H | OEt | Me | |
| 1.129 | 6-Cl | H | OEt | Et | |
| 1.130 | 6-Br | H | OEt | n-Propyl | |
| 1.131 | 6-Cl | H | OEt | n-Propyl | |
| 1.132 | H | 7-Cl | OEt | n-Propyl | |
| 1.133 | H | 7-I | OEt | n-Propyl | |
| 1.134 | 6-Br | H | OEt |  | |
| 1.135 | 6-Cl | H | OEt |  | |
| 1.136 | H | 7-Cl | OEt |  | |
| 1.137 | 6-Br | H | OEt | n-Butyl | |
| 1.138 | 6-Cl | H | OEt | n-Butyl | |
| 1.139 | H | 7-Cl | OEt | n-Butyl | |
| 1.140 | H | 7-I | OEt | n-Butyl | |
| 1.141 | 6-Br | H | OEt | i-Butyl | |
| 1.142 | 6-Cl | H | OEt | i-Butyl | |
| 1.143 | 6-Br | H | OEt |  | |
| 1.144 | 6-Cl | H | OEt | | |
| 1.145 | H | 7-Cl | OEt | | |

TABLE 1-continued

A = Phenyl

| cmpd. No. | R₁ | R₂ | R₃ | R₄ | phys. data m.p. °C. |
|---|---|---|---|---|---|
| 1.146 | 6-Br | H | OEt | (cyclopropyl-Me) | |
| 1.147 | 6-Cl | H | OEt | (cyclopropyl-Me) | |
| 1.148 | 6-Br | H | OEt | Cyclobutyl | |
| 1.149 | 6-Br | H | OEt | n-Pentyl | |
| 1.150 | 6-Cl | H | OEt | n-Pentyl | |
| 1.151 | H | 7-Cl | OEt | n-Pentyl | |
| 1.152 | 6-Br | H | OEt | Cyclopentyl | |
| 1.153 | 6-Br | H | OEt | n-Hexyl | |
| 1.154 | 6-Br | H | OEt | Cyclohexyl | |
| 1.155 | 6-Br | H | OEt | Phenyl | |
| 1.156 | 6-Br | H | OEt | 4-Chlorophenyl | |
| 1.157 | 6-Cl | H | OEt | 4-Chlorophenyl | |
| 1.158 | 6-Br | H | OEt | 4-Phenoxyphenyl | |
| 1.159 | 6-Br | H | O-n-Propyl | Me | |
| 1.160 | 6-Cl | H | O-n-Propyl | Et | |
| 1.161 | 6-Br | H | O-n-Propyl | n-Propyl | |
| 1.162 | 6-Cl | H | O-n-Propyl | n-Propyl | |
| 1.163 | H | 7-Cl | O-n-Propyl | n-Propyl | |
| 1.164 | H | 7-I | O-n-Propyl | n-Propyl | |
| 1.165 | 6-Br | H | O-n-Propyl | cyclopropyl | |
| 1.166 | 6-Cl | H | O-n-Propyl | cyclopropyl | |
| 1.167 | H | 7-Cl | O-n-Propyl | cyclopropyl | |
| 1.168 | 6-Br | H | O-n-Propyl | n-Butyl | |
| 1.169 | 6-Cl | H | O-n-Propyl | n-Butyl | |
| 1.170 | H | 7-Cl | O-n-Propyl | n-Butyl | |
| 1.171 | H | 7-I | O-n-Propyl | n-Butyl | |
| 1.172 | 6-Br | H | O-n-Propyl | i-Butyl | |
| 1.173 | 6-Cl | H | O-n-Propyl | i-Butyl | |
| 1.174 | 6-Br | H | O-n-Propyl | (cyclopropyl-Me) | |
| 1.175 | 6-Cl | H | O-n-Propyl | (cyclopropyl-Me) | |
| 1.176 | H | 7-Cl | O-n-Propyl | (cyclopropyl-Me) | |
| 1.177 | 6-Br | H | O-n-Propyl | (cyclopropyl-Me) | |
| 1.178 | 6-Cl | H | O-n-Propyl | (cyclopropyl-Me) | |
| 1.179 | 6-Br | H | O-n-Propyl | Cyclobutyl | |
| 1.180 | 6-Br | H | O-n-Propyl | n-Pentyl | |
| 1.181 | 6-Cl | H | o-n-Propyl | n-Pentyl | |
| 1.182 | H | 7-Cl | O-n-Propyl | n-Pentyl | |
| 1.183 | 6-Br | H | O-n-Propyl | Cyclopentyl | |
| 1.184 | 6-Br | H | O-n-Prpyl | n-Hexyl | |
| 1.185 | 6-Br | H | O-n-Prpyl | Cyclohexyl | |
| 1.186 | 6-Br | H | O-n-Prpyl | Phenyl | |
| 1.187 | 6-Br | H | O-n-Prpyl | 4-Chlorophenyl | |
| 1.188 | 6-Cl | H | O-n-Prpyl | 4-Chlorophenyl | |
| 1.189 | 6-Br | H | O-n-Prpyl | 4-Phenoxyphenyl | |
| 1.190 | 6-Br | H | Et | $CH_2OMe$ | |
| 1.191 | 6-Cl | H | Et | $CH_2OMe$ | |
| 1.192 | 6-Br | H | n-Prpyl | $CH_2OMe$ | |
| 1.193 | 6-Cl | H | n-Prpyl | $CH_2OMe$ | |
| 1.194 | H | 7-Cl | n-Prpyl | $CH_2OMe$ | |
| 1.195 | 6-Br | H | n-Butyl | $CH_2OMe$ | |
| 1.196 | 6-Cl | H | n-Butyl | $CH_2OMe$ | |
| 1.197 | 6-Br | H | cyclopropyl-$CH_2$ | $CH_2OMe$ | |
| 1.198 | 6-Br | H | n-Pentyl | $CH_2OMe$ | |
| 1.199 | 6-Br | H | Et | $CH_2OEt$ | |
| 1.200 | 6-Cl | H | Et | $CH_2OEt$ | |
| 1.201 | 6-Br | H | n-Propyl | $CH_2OEt$ | |
| 1.202 | 6-Cl | H | n-Propyl | $CH_2OEt$ | |
| 1.203 | H | 7-Cl | n-Propyl | $CH_2OEt$ | |
| 1.204 | 6-Br | H | n-Butyl | $CH_2OEt$ | |
| 1.205 | 6-Cl | H | n-Butyl | $CH_2OEt$ | |
| 1.206 | 6-Br | H | cyclopropyl-$CH_2$ | $CH_2OEt$ | |
| 1.207 | 6-Br | H | n-Pentyl | $CH_2OEt$ | |
| 1.208 | 6-Br | H | n-Propyl | $CH_2CN$ | |
| 1.209 | 6-Br | H | n-Butyl | $CH_2CN$ | |
| 1.210 | 6-Br | H | n-Propyl | t-Butyl | |
| 1.211 | 6-Br | H | n-Propyl | t-Butyl | |

TABLE 1-continued

A = Phenyl

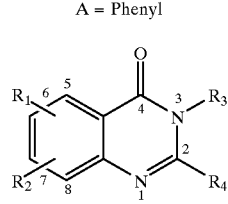

| cmpd. No. | $R_1$ | $R_2$ | $R_3$ | $R_4$ | phys. data m.p. °C. |
|---|---|---|---|---|---|
| 1.212 | 6-Cl | H | n-Propyl | $CF_3$ | |
| 1.213 | 6-Br | H | n-Propyl | $CF_3$ | |
| 1.214 | 6-Br | H | n-Butyl | $CF_3$ | |

TABELLE 2

A = Pyridyl

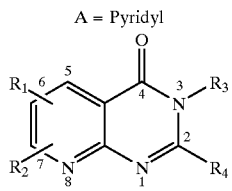

| cmpd. No. | $R_1$ | $R_2$ | $R_3$ | $R_4$ | phys. data m.p. °C. |
|---|---|---|---|---|---|
| 2.1 | 6-Br | H | Me | Me | |
| 2.2 | 6-Cl | H | Me | Et | |
| 2.3 | 6-Br | H | Me | n-Propyl | |
| 2.4 | 6-Cl | H | Me | n-Propyl | |
| 2.5 | 6-Br | H | Me | n-Butyl | |
| 2.6 | 6-Cl | H | Me | n-Butyl | |
| 2.7 | 6-Br | H | Me | i-Butyl | |
| 2.8 | 6-Cl | H | Me | i-Butyl | |
| 2.9 | 6-Br | H | Me | n-Pentyl | |
| 2.10 | 6-Br | H | Me |  | |
| 2.11 | 6-Cl | H | Me |  | |
| 2.12 | 6-Br | H | Et | Me | |
| 2.13 | 6-Cl | H | Et | Et | |
| 2.14 | 6-Br | H | Et | n-Propyl | |
| 2.15 | 6-Cl | H | Et | n-Propyl | |
| 2.16 | 6-Br | H | Et | n-Butyl | |
| 2.17 | 6-Cl | H | Et | n-Butyl | |
| 2.18 | 6-Br | H | Et | i-Butyl | |
| 2.19 | 6-Cl | H | Et | i-Butyl | |
| 2.20 | 6-Br | H | Et | n-Pentyl | |
| 2.21 | 6-Br | H | Et |  | |
| 2.22 | 6-Cl | H | Et |  | |
| 2.23 | 6-Br | H | n-Propyl | Me | |
| 2.24 | 6-Cl | H | n-Propyl | Et | |
| 2.25 | 6-Br | H | n-Propyl | n-Propyl | |

TABELLE 2-continued

A = Pyridyl

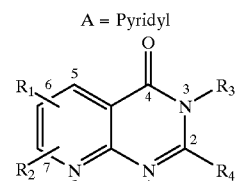

| cmpd. No. | $R_1$ | $R_2$ | $R_3$ | $R_4$ | phys. data m.p. °C. |
|---|---|---|---|---|---|
| 2.26 | 6-Cl | H | n-Propyl | n-Propyl | |
| 2.27 | 7-I | H | n-Propyl | n-Propyl | |
| 2.28 | 6-Br | H | n-Propyl |  | |
| 2.29 | 6-Cl | H | n-Propyl |  | |
| 2.30 | 6-Br | H | n-Propyl | n-Butyl | Oil, $^1$H-NMR |
| 2.31 | 6-Cl | H | n-Propyl | n-Butyl | |
| 2.32 | 6-I | H | n-Propyl | n-Butyl | |
| 2.33 | 6-Br | H | n-Propyl | i-Butyl | |
| 2.34 | 6-Cl | H | n-Propyl | i-Butyl | |
| 2.35 | 6-Br | H | n-Propyl |  | |
| 2.36 | 6-Cl | H | n-Propyl |  | |
| 2.37 | 6-Br | H | n-Propyl |  | |
| 2.38 | 6-Cl | H | n-Propyl |  | |
| 2.39 | 6-Br | H | n-Propyl | Cyclobutyl | |
| 2.40 | 6-Br | H | n-Propyl | n-Pentyl | |
| 2.41 | 6-Cl | H | n-Propyl | n-Pentyl | |
| 2.42 | 6-Br | H | n-Propyl | Cyclopentyl | |
| 2.43 | 6-Br | H | n-Propyl | n-Hexyl | |
| 2.44 | 6-Br | H | n-Propyl | Cyclohexyl | |
| 2.45 | 6-Br | H | n-Propyl | Phenyl | |
| 2.46 | 6-Br | H | n-Propyl | 4-Chloro-phenyl | |
| 2.47 | 6-Cl | H | n-Propyl | 4-Chloro-phenyl | |
| 2.48 | 6-Br | H | n-Propyl | 4-Phenoxy-phenyl | |
| 2.49 | 6-Br | H | n-Butyl | Me | |
| 2.50 | 6-Cl | H | n-Butyl | Et | |
| 2.51 | 6-Br | H | n-Butyl | n-Propyl | |
| 2.52 | 6-Cl | H | n-Butyl | n-Propyl | |
| 2.53 | H | 7-Cl | n-Butyl | n-Propyl | |
| 2.54 | H | 7-I | n-Butyl | n-Propyl | |
| 2.55 | 6-Br | H | n-Butyl |  | |

TABELLE 2-continued

A = Pyridyl

Structure: Pyrido-pyrimidinone with R$_1$ at position 6, R$_2$ at position 7, N at position 8, N$_1$, C$_2$-R$_4$, N$_3$-R$_3$, C$_4$=O, position 5.

| cmpd. No. | R$_1$ | R$_2$ | R$_3$ | R$_4$ | phys. data m.p. °C. |
|---|---|---|---|---|---|
| 2.56 | 6-Cl | H | n-Butyl | cyclopropyl | |
| 2.57 | H | 7-Cl | n-Butyl | cyclopropyl | |
| 2.58 | 6-Br | H | n-Butyl | n-Butyl | |
| 2.59 | 6-Cl | H | n-Butyl | n-Butyl | |
| 2.60 | 6-I | H | n-Butyl | n-Butyl | |
| 2.61 | 6-Br | H | n-Butyl | i-Butyl | |
| 2.62 | 6-Cl | H | n-Butyl | i-Butyl | |
| 2.63 | 6-Br | H | n-Butyl | methylcyclopropyl | |
| 2.64 | 6-Cl | H | n-Butyl | methylcyclopropyl | |
| 2.65 | 6-I | H | n-Butyl | methylcyclopropyl | |
| 2.66 | 6-Br | H | n-Butyl | Me-methylcyclopropyl | |
| 2.67 | 6-Cl | H | n-Butyl | Me-methylcyclopropyl | |
| 2.68 | 6-Br | H | n-Butyl | Cyclobutyl | |
| 2.69 | 6-Br | H | n-Butyl | n-Pentyl | |
| 2.70 | 6-Cl | H | n-Butyl | n-Pentyl | |
| 2.71 | 6-Br | H | n-Butyl | Cyclopentyl | |
| 2.72 | 6-Br | H | n-Butyl | n-Hexyl | |
| 2.73 | 6-Br | H | n-Butyl | Cyclohexyl | |
| 2.74 | 6-Br | H | n-Butyl | Phenyl | |
| 2.75 | 6-Br | H | n-Butyl | 4-Chlorophenyl | |
| 2.76 | 6-Cl | H | n-Butyl | 4-Chlorophenyl | |
| 2.77 | 6-Br | H | n-Butyl | 4-Phenoxyphenyl | |
| 2.78 | 6-Br | H | i-Butyl | n-Propyl | |
| 2.79 | 6-Cl | H | i-Butyl | n-Propyl | |
| 2.80 | 6-Br | H | i-Butyl | n-Butyl | |
| 2.81 | 6-Cl | H | i-Butyl | n-Butyl | |
| 2.82 | 6-Br | H | cyclopropyl-CH$_2$ | n-Propyl | |
| 2.83 | 6-Cl | H | cyclopropyl-CH$_2$ | n-Propyl | |
| 2.84 | 6-Br | H | methylcyclopropyl-CH$_2$ | n-Propyl | |
| 2.85 | 6-Br | H | methylcyclopropyl-CH$_2$ | n-Butyl | |
| 2.86 | 6-Br | H | n-Pentyl | Me | |
| 2.87 | 6-Cl | H | n-Pentyl | Et | |
| 2.88 | 6-Br | H | n-Pentyl | n-Propyl | |
| 2.89 | 6-Cl | H | n-Pentyl | n-Propyl | |
| 2.90 | 6-Br | H | n-Pentyl | cyclopropyl | |
| 2.91 | 6-Cl | H | n-Pentyl | cyclopropyl | |
| 2.92 | 6-Br | H | n-Pentyl | n-Butyl | |
| 2.93 | 6-Cl | H | n-Pentyl | n-Butyl | |
| 2.94 | 6-I | H | n-Pentyl | n-Butyl | |
| 2.95 | 6-Br | H | n-Pentyl | i-Butyl | |
| 2.96 | 6-Cl | H | n-Pentyl | i-Butyl | |
| 2.97 | 6-Br | H | n-Pentyl | methylcyclopropyl | |
| 2.98 | 6-Cl | H | n-Pentyl | methylcyclopropyl | |
| 2.99 | 6-Br | H | n-Pentyl | Me-methylcyclopropyl | |
| 2.100 | 6-Cl | H | n-Pentyl | Me-methylcyclopropyl | |
| 2.101 | 6-Br | H | n-Pentyl | Cyclobutyl | |
| 2.102 | 6-Br | H | n-Pentyl | n-Pentyl | |
| 2.103 | 6-Cl | H | n-Pentyl | n-Pentyl | |
| 2.104 | 6-Br | H | n-Pentyl | Cyclopentyl | |

TABELLE 2-continued

A = Pyridyl

Structure: R1 at position 6, R2 at position 7, N at 8, N1, R4 at C2, N3-R3, C4=O, positions 5,6 on benzene ring fused.

| cmpd. No. | R₁ | R₂ | R₃ | R₄ | phys. data m.p. °C. |
|---|---|---|---|---|---|
| 2.105 | 6-Br | H | n-Pentyl | n-Hexyl | |
| 2.106 | 6-Br | H | n-Pentyl | Cyclohexyl | |
| 2.107 | 6-Br | H | n-Pentyl | Phenyl | |
| 2.108 | 6-Br | H | n-Pentyl | 4-Chloro-phenyl | |
| 2.109 | 6-Cl | H | n-Pentyl | 4-Chloro-phenyl | |
| 2.110 | 6-Br | H | n-Pentyl | 4-Phenoxy-phenyl | |
| 2.111 | 6-Br | H | OEt | Me | |
| 2.112 | 6-Cl | H | OEt | Et | |
| 2.113 | 6-Br | H | OEt | n-Propyl | |
| 2.114 | 6-Cl | H | OEt | n-Propyl | |
| 2.115 | 6-Br | H | OEt | cyclopropyl | |
| 2.116 | 6-Cl | H | OEt | cyclopropyl | |
| 2.117 | 6-Br | H | OEt | n-Butyl | |
| 2.118 | 6-Cl | H | OEt | n-Butyl | |
| 2.119 | 6-I | H | OEt | n-Butyl | |
| 2.120 | 6-Br | H | OEt | i-Butyl | |
| 2.121 | 6-Cl | H | OEt | i-Butyl | |
| 2.122 | 6-Br | H | OEt | cyclopropylmethyl | |
| 2.123 | 6-Cl | H | OEt | cyclopropylmethyl | |
| 2.124 | 6-Br | H | OEt | (2-methylcyclopropyl) | |
| 2.125 | 6-Cl | H | OEt | (2-methylcyclopropyl) | |
| 2.126 | 6-Br | H | OEt | Cyclobutyl | |
| 2.127 | 6-Br | H | OEt | n-Pentyl | |
| 2.128 | 6-Cl | H | OEt | n-Pentyl | |
| 2.129 | 6-Br | H | OEt | Cyclopentyl | |
| 2.130 | 6-Br | H | OEt | n-Hexyl | |
| 2.131 | 6-Br | H | OEt | Cyclohexyl | |
| 2.132 | 6-Br | H | OEt | Phenyl | |
| 2.133 | 6-Br | H | OEt | 4-Chloro-phenyl | |
| 2.134 | 6-Cl | H | OEt | 4-Chloro-phenyl | |
| 2.135 | 6-Br | H | OEt | 4-Phenoxy-phenyl | |
| 2.136 | 6-Br | H | O-n-Propyl | Me | |
| 2.137 | 6-Cl | H | O-n-Propyl | Et | |
| 2.138 | 6-Br | H | O-n-Propyl | n-Propyl | |
| 2.139 | 6-Cl | H | O-n-Propyl | n-Propyl | |
| 2.140 | 6-Br | H | O-n-Propyl | cyclopropyl | |
| 2.141 | 6-Cl | H | O-n-Propyl | cyclopropyl | |
| 2.142 | 6-Br | H | O-n-Propyl | n-Butyl | |
| 2.143 | 6-Cl | H | O-n-Propyl | n-Butyl | |
| 2.144 | 6-Br | H | O-n-Propyl | i-Butyl | |
| 2.145 | 6-Cl | H | O-n-Propyl | i-Butyl | |
| 2.146 | 6-Br | H | O-n-Propyl | cyclopropylmethyl | |
| 2.147 | 6-Cl | H | O-n-Propyl | cyclopropylmethyl | |
| 2.148 | 6-Br | H | O-n-Propyl | (2-methylcyclopropyl) | |
| 2.149 | 6-Cl | H | O-n-Propyl | (2-methylcyclopropyl) | |
| 2.150 | 6-Br | H | O-n-Propyl | Cyclobutyl | |
| 2.151 | 6-Br | H | O-n-Propyl | n-Pentyl | |
| 2.152 | 6-Cl | H | O-n-Propyl | n-Pentyl | |
| 2.153 | 6-Br | H | O-n-Propyl | Cyclopentyl | |
| 2.154 | 6-Br | H | O-n-Propyl | n-Hexyl | |
| 2.155 | 6-Br | H | O-n-Propyl | Cyclohexyl | |
| 2.156 | 6-Br | H | O-n-Propyl | Phenyl | |
| 2.157 | 6-Br | H | O-n-Propyl | 4-Chloro-phenyl | |
| 2.158 | 6-Cl | H | O-n-Propyl | 4-Chloro-phenyl | |
| 2.159 | 6-Br | H | O-n-Propyl | 4-Phenoxy-phenyl | |
| 2.160 | 6-Br | H | Et | $CH_2OMe$ | |
| 2.161 | 6-Cl | H | Et | $CH_2OMe$ | |
| 2.162 | 6-Br | H | n-Propyl | $CH_2OMe$ | |
| 2.163 | 6-Cl | H | n-Propyl | $CH_2OMe$ | |
| 2.164 | 6-Br | H | n-Butyl | $CH_2OMe$ | |
| 2.165 | 6-Cl | H | n-Butyl | $CH_2OMe$ | |
| 2.166 | 6-Br | H | cyclopropyl-$CH_2$ | $CH_2OMe$ | |
| 2.167 | 6-Br | H | n-Pentyl | $CH_2OMe$ | |
| 2.168 | 6-Br | H | Et | $CH_2OEt$ | |

TABELLE 2-continued

A = Pyridyl

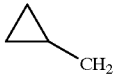

| cmpd. No. | R₁ | R₂ | R₃ | R₄ | phys. data m.p. °C. |
|---|---|---|---|---|---|
| 2.169 | 6-Cl | H | Et | CH₂OEt | |
| 2.170 | 6-Br | H | n-Propyl | CH₂OEt | |
| 2.171 | 6-Cl | H | n-Propyl | CH₂OEt | |
| 2.172 | 6-Br | H | n-Butyl | CH₂OEt | |
| 2.173 | 6-Cl | H | n-Butyl | CH₂OEt | |
| 2.174 | 6-Br | H | cyclopropyl-CH₂ | CH₂OEt | |
| 2.175 | 6-Br | H | n-Pentyl | CH₂OEt | |
| 2.176 | 6-Br | H | n-Propyl | CH₂CN | |
| 2.177 | 6-Br | H | n-Butyl | CH₂CN | |
| 2.178 | 6-Br | H | n-Propyl | t-Butyl | |
| 2.179 | 6-Br | H | n-Propyl | t-Butyl | |
| 2.180 | 6-Br | H | n-Propyl | CF₃ | |
| 2.181 | 6-Br | H | n-Butyl | CF₃ | |

TABELLE 3

A = Thienyl[2.3-d]

| cmpd. No. | R₁ | R₂ | R₃ | R₄ | phys. data m.p. °C. |
|---|---|---|---|---|---|
| 3.1 | Cl | H | Me | Me | 139–141 |
| 3.2 | Cl | H | Me | Et | |
| 3.3 | Br | H | Me | n-Propyl | |
| 3.4 | Cl | H | Me | n-Propyl | |
| 3.5 | Br | H | Me | n-Butyl | |
| 3.6 | Cl | H | Me | n-Butyl | 63–65 |
| 3.7 | Br | H | Me | i-Butyl | |
| 3.8 | Cl | H | Me | i-Butyl | 87–89 |
| 3.9 | Br | H | Me | n-Pentyl | |
| 3.10 | Br | H | Me | cyclopropyl-CH₂ | |
| 3.11 | Cl | H | Me | cyclopropyl-CH₂ | |
| 3.12 | Br | H | Et | Me | |
| 3.13 | Cl | H | Et | Et | |
| 3.14 | Br | H | Et | n-Propyl | |
| 3.15 | Cl | H | Et | n-Propyl | 80–82 |
| 3.16 | Br | H | Et | n-Butyl | |
| 3.17 | Cl | H | Et | n-Butyl | Oil, ¹H-NMR |
| 3.18 | Br | H | Et | i-Butyl | |
| 3.19 | Cl | H | Et | i-Butyl | |
| 3.20 | Br | H | Et | n-Pentyl | |

TABELLE 3-continued

A = Thienyl[2.3-d]

| cmpd. No. | R₁ | R₂ | R₃ | R₄ | phys. data m.p. °C. |
|---|---|---|---|---|---|
| 3.21 | Br | H | Et | cyclopropyl-CH₂ | |
| 3.22 | Cl | H | Et | cyclopropyl-CH₂ | |
| 3.23 | Br | H | n-Propyl | Me | |
| 3.24 | Cl | H | n-Propyl | Et | |
| 3.25 | Br | H | n-Propyl | n-Propyl | |
| 3.26 | Cl | H | n-Propyl | n-Propyl | 74–76 |
| 3.27 | I | H | n-Propyl | n-Propyl | |
| 3.28 | Br | H | n-Propyl | cyclopropyl | |
| 3.29 | Cl | H | n-Propyl | cyclopropyl | |
| 3.30 | Br | H | n-Propyl | n-Butyl | 63–66 |
| 3.31 | Cl | H | n-Propyl | n-Butyl | 67–69 |
| 3.32 | I | H | n-Propyl | n-Butyl | |
| 3.33 | Br | H | n-Propyl | i-Butyl | |
| 3.34 | Cl | H | n-Propyl | i-Butyl | Oil, ¹H-NMR |
| 3.35 | Br | H | n-Propyl | cyclopropyl-CH₂ | |
| 3.36 | Cl | H | n-Propyl | cyclopropyl-CH₂ | Oil, ¹H-NMR |
| 3.37 | Br | H | n-Propyl | 2-methylcyclopropyl | |
| 3.38 | Cl | H | n-Propyl | 2-methylcyclopropyl | |
| 3.39 | Br | H | n-Propyl | Cyclobutyl | |
| 3.40 | Br | H | n-Propyl | n-Pentyl | |
| 3.41 | Cl | H | n-Propyl | n-Pentyl | |
| 3.42 | Br | H | n-Propyl | Cyclopentyl | |
| 3.43 | Br | H | n-Propyl | n-Hexyl | |
| 3.44 | Br | H | n-Propyl | Cyclohexyl | |
| 3.45 | Br | H | n-Propyl | Phenyl | |
| 3.46 | Br | H | n-Propyl | 4-Chloro-phenyl | |
| 3.47 | Cl | H | n-Propyl | 4-Chloro-phenyl | 126–128 |

TABELLE 3-continued

A = Thienyl[2.3-d]

| cmpd. No. | $R_1$ | $R_2$ | $R_3$ | $R_4$ | phys. data m.p. °C. |
|---|---|---|---|---|---|
| 3.48 | Br | H | n-Propyl | 4-Phenoxy-phenyl | |
| 3.49 | Br | H | n-Butyl | Me | |
| 3.50 | Cl | H | n-Butyl | Et | |
| 3.51 | Br | H | n-Butyl | n-Propyl | |
| 3.52 | Cl | H | n-Butyl | n-Propyl | Oil |
| 3.53 | I | H | n-Butyl | n-Propyl | |
| 3.54 | I | H | n-Butyl | n-Propyl | |
| 3.55 | Br | H | n-Butyl |  | |
| 3.56 | Cl | H | n-Butyl |  | 54–56 |
| 3.57 | I | H | n-Butyl |  | |
| 3.58 | Br | H | n-Butyl | n-Butyl | Oil |
| 3.59 | Cl | H | n-Butyl | n-Butyl | 57–58 |
| 3.60 | I | H | n-Butyl | n-Butyl | |
| 3.61 | Br | H | n-Butyl | i-Butyl | |
| 3.62 | Cl | H | n-Butyl | i-Butyl | |
| 3.63 | Br | H | n-Butyl |  | |
| 3.64 | Cl | H | n-Butyl |  | |
| 3.65 | I | H | n-Butyl | 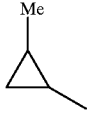 | |
| 3.66 | Br | H | n-Butyl | 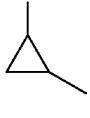 | |
| 3.67 | Cl | H | n-Butyl | 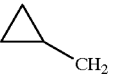 | |
| 3.68 | Br | H | n-Butyl | Cyclobutyl | |
| 3.69 | Br | H | n-Butyl | n-Pentyl | |
| 3.70 | Cl | H | n-Butyl | n-Pentyl | |
| 3.71 | Br | H | n-Butyl | Cyclopentyl | |
| 3.72 | Br | H | n-Butyl | n-Hexyl | |
| 3.73 | Br | H | n-Butyl | Cyclohexyl | |
| 3.74 | Cl | H | n-Butyl | Phenyl | |
| 3.75 | Br | H | n-Butyl | 4-Chloro-phenyl | |
| 3.76 | Cl | H | n-Butyl | 4-Chloro-phenyl | |
| 3.77 | Br | H | n-Butyl | 4-Phenoxy-phenyl | |
| 3.78 | Br | H | i-Butyl | n-Propyl | |
| 3.79 | Cl | H | i-Butyl | n-Propyl | Oil, $^1$H-NMR |
| 3.80 | Br | H | i-Butyl | n-Butyl | |
| 3.81 | Cl | H | i-Butyl | n-Butyl | |
| 3.82 | Br | H | 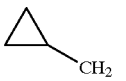 | n-Propyl | |
| 3.83 | Cl | H |  | n-Propyl | |
| 3.84 | Cl | H | 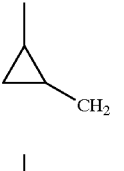 | n-Propyl | |
| 3.85 | Br | H |  | n-Butyl | |
| 3.86 | Br | H | n-Pentyl | Me | |
| 3.87 | Cl | H | n-Pentyl | Et | |
| 3.88 | Br | H | n-Pentyl | n-Propyl | |
| 3.89 | Cl | H | n-Pentyl | n-Propyl | |
| 3.90 | Br | H | n-Pentyl |  | |
| 3.91 | Cl | H | n-Pentyl |  | |
| 3.92 | Br | H | n-Pentyl | n-Butyl | |
| 3.93 | Cl | H | n-Pentyl | n-Butyl | |
| 3.94 | I | H | n-Pentyl | n-Butyl | |
| 3.95 | Br | H | n-Pentyl | i-Butyl | |
| 3.96 | Cl | H | n-Pentyl | i-Butyl | |
| 3.97 | Br | H | n-Pentyl |  | |
| 3.98 | Cl | H | n-Pentyl | | |
| 3.99 | Br | H | n-Pentyl |  | |

TABELLE 3-continued

A = Thienyl[2,3-d]

| cmpd. No. | $R_1$ | $R_2$ | $R_3$ | $R_4$ | phys. data m.p. °C. |
|---|---|---|---|---|---|
| 3.100 | Cl | H | n-Pentyl | (2-methylcyclopropyl) | |
| 3.101 | Cl | H | n-Pentyl | Cyclobutyl | |
| 3.102 | Br | H | n-Pentyl | n-Pentyl | |
| 3.103 | Cl | H | n-Pentyl | n-Pentyl | |
| 3.104 | Cl | H | n-Pentyl | Cyclopentyl | |
| 3.105 | Br | H | n-Pentyl | n-Hexyl | |
| 3.106 | Cl | H | n-Pentyl | Cyclohexyl | |
| 3.107 | Br | H | n-Pentyl | Phenyl | |
| 3.108 | Br | H | n-Pentyl | 4-Chloro-phenyl | |
| 3.109 | Cl | H | n-Pentyl | 4-Chloro-phenyl | |
| 3.110 | Br | H | n-Pentyl | 4-Phenoxy-phenyl | |
| 3.111 | Br | H | OEt | Me | |
| 3.112 | Cl | H | OEt | Et | |
| 3.113 | Br | H | OEt | n-Propyl | |
| 3.114 | Cl | H | OEt | n-Propyl | |
| 3.115 | Br | H | OEt | cyclopropyl | |
| 3.116 | Cl | H | OEt | cyclopropyl | |
| 3.117 | Br | H | OEt | n-Butyl | 75–77 |
| 3.118 | Cl | H | OEt | n-Butyl | 66–69 |
| 3.119 | I | H | OEt | n-Butyl | |
| 3.120 | Br | H | OEt | i-Butyl | |
| 3.121 | Cl | H | OEt | i-Butyl | |
| 3.122 | Br | H | OEt | (cyclopropylmethyl) | |
| 3.123 | Cl | H | OEt | (cyclopropylmethyl) | |
| 3.124 | Br | H | OEt | (2-methylcyclopropyl) | |
| 3.125 | Cl | H | OEt | (2-methylcyclopropyl) | |
| 3.126 | Br | H | OEt | Cyclobutyl | |
| 3.127 | Br | H | OEt | n-Pentyl | |
| 3.128 | Cl | H | OEt | n-Pentyl | |
| 3.129 | Br | H | OEt | Cyclopentyl | |
| 3.130 | Br | H | OEt | n-Hexyl | |
| 3.131 | Br | H | OEt | Cyclohexyl | |
| 3.132 | Br | H | OEt | Phenyl | |
| 3.133 | Br | H | OEt | 4-Chloro-phenyl | |
| 3.134 | Cl | H | OEt | 4-Chloro-phenyl | |
| 3.135 | Cl | H | OEt | 4-Phenoxy-phenyl | |
| 3.136 | Br | H | O-n-Propyl | Me | |
| 3.137 | Cl | H | O-n-Propyl | Et | |
| 3.138 | Br | H | O-n-Propyl | n-Propyl | |
| 3.139 | Cl | H | O-n-Propyl | n-Propyl | |
| 3.140 | Br | H | O-n-Propyl | cyclopropyl | |
| 3.141 | Cl | H | O-n-Propyl | cyclopropyl | |
| 3.142 | Br | H | O-n-Propyl | n-Butyl | |
| 3.143 | Cl | H | O-n-Propyl | n-Butyl | |
| 3.144 | Br | H | O-n-Propyl | i-Butyl | |
| 3.145 | Cl | H | O-n-Propyl | i-Butyl | |
| 3.146 | Br | H | O-n-Propyl | (cyclopropylmethyl) | |
| 3.147 | Cl | H | O-n-Propyl | (cyclopropylmethyl) | |
| 3.148 | Br | H | O-n-Propyl | (2-methylcyclopropyl) | |
| 3.149 | Cl | H | O-n-Propyl | (2-methylcyclopropyl) | |
| 3.150 | Br | H | O-n-Propyl | Cyclobutyl | |
| 3.151 | Br | H | O-n-Propyl | n-Pentyl | |
| 3.152 | Cl | H | O-n-Propyl | n-Pentyl | |
| 3.153 | Br | H | O-n-Propyl | Cyclopentyl | |
| 3.154 | Cl | H | O-n-Propyl | n-Hexyl | |
| 3.155 | Br | H | O-n-Propyl | Cyclohexyl | |
| 3.156 | Cl | H | O-n-Propyl | Phenyl | |
| 3.157 | Br | H | O-n-Propyl | 4-Chloro-phenyl | |
| 3.158 | Cl | H | O-n-Propyl | 4-Chloro-phenyl | |
| 3.159 | Br | H | O-n-Propyl | 4-Phenoxy-phenyl | |
| 3.160 | Br | H | Et | $CH_2OMe$ | |
| 3.161 | Cl | H | Et | $CH_2OMe$ | |

TABELLE 3-continued

A = Thienyl[2.3-d]

Structure: Thienopyrimidinone with R₁ at position 6, R₂ at position 5, R₃ on N3, R₄ on C2, S at position with 6, carbonyl at 4.

| cmpd. No. | R₁ | R₂ | R₃ | R₄ | phys. data m.p. ° C. |
|---|---|---|---|---|---|
| 3.162 | Br | H | n-Propyl | CH₂OMe | |
| 3.163 | Cl | H | n-Propyl | CH₂OMe | Oil, ¹H-NMR |
| 3.164 | Br | H | n-Butyl | CH₂OMe | |
| 3.165 | Cl | H | n-Butyl | CH₂OMe | |
| 3.166 | Br | H | cyclopropyl-CH₂ | CH₂OMe | |
| 3.167 | Br | H | n-Pentyl | CH₂OMe | |
| 3.168 | Br | H | Et | CH₂OEt | |
| 3.169 | Cl | H | Et | CH₂OEt | |
| 3.170 | Br | H | n-Propyl | CH₂OEt | |
| 3.171 | Cl | H | n-Propyl | CH₂OEt | 40–41 |
| 3.172 | Br | H | n-Butyl | CH₂OEt | |
| 3.173 | Cl | H | n-Butyl | CH₂OEt | |
| 3.174 | Br | H | cyclopropyl-CH₂ | CH₂OEt | |
| 3.175 | Br | H | n-Pentyl | CH₂OEt | |
| 3.176 | Br | H | n-Propyl | CH₂CN | |
| 3.177 | Cl | H | n-Butyl | CH₂CN | |
| 3.178 | Br | H | n-Propyl | t-Butyl | |
| 3.179 | Cl | H | n-Propyl | t-Butyl | |
| 3.180 | Br | H | n-Propyl | CF₃ | |
| 3.181 | Cl | H | n-Butyl | CF₃ | |
| 3.182 | Cl | H | n-Pentyl | CF₃ | |
| 3.183 | Cl | Cl | n-Propyl | n-Propyl | |
| 3.184 | Cl | Cl | n-Butyl | n-Propyl | |
| 3.185 | Br | Br | n-Propyl | n-Butyl | |
| 3.186 | Br | Br | n-Butyl | n-Butyl | |

TABELLE 4

A = Thienyl[3.2-d]

Structure: Thienopyrimidinone with R₁ at position 7, R₂ at position 6, S at position 5, R₃ on N3, R₄ on C2.

| Cmpd. No. | R₁ | R₂ | R₃ | R₄ | phys. data |
|---|---|---|---|---|---|
| 4.1 | Br | H | Me | Me | |
| 4.2 | H | Cl | Me | Et | |
| 4.3 | Br | H | Me | n-Propyl | |
| 4.4 | H | Cl | Me | n-Propyl | |
| 4.5 | H | Cl | Me | n-Propyl | |
| 4.6 | Br | H | Me | n-Butyl | |
| 4.7 | H | Cl | Me | n-Butyl | |
| 4.8 | H | Cl | Me | n-Butyl | |
| 4.9 | Br | H | Me | i-Butyl | |
| 4.10 | H | Cl | Me | i-Butyl | |
| 4.11 | Br | H | Me | n-Pentyl | |
| 4.12 | Br | H | Me | cyclopropyl-CH₂ | |
| 4.13 | H | Cl | Me | cyclopropyl-CH₂ | |
| 4.14 | Br | H | Et | Me | |
| 4.15 | H | Cl | Et | Et | |
| 4.16 | Br | H | Et | n-Propyl | |
| 4.17 | H | Cl | Et | n-Propyl | |
| 4.18 | H | Cl | Et | n-Propyl | |
| 4.19 | Br | H | Et | n-Butyl | |
| 4.20 | H | Cl | Et | n-Butyl | |
| 4.21 | H | Cl | Et | n-Butyl | |
| 4.22 | Br | H | Et | i-Butyl | |
| 4.23 | H | Cl | Et | i-Butyl | |
| 4.24 | Br | H | Et | n-Pentyl | |
| 4.25 | Br | H | Et | cyclopropyl-CH₂ | |
| 4.26 | H | Cl | Et | cyclopropyl-CH₂ | |
| 4.27 | Br | H | n-Propyl | Me | |
| 4.28 | H | Cl | n-Propyl | Et | |
| 4.29 | Br | H | n-Propyl | n-Propyl | |
| 4.30 | H | Cl | n-Propyl | n-Propyl | |
| 4.31 | H | Cl | n-Propyl | n-Propyl | |
| 4.32 | H | I | n-Propyl | n-Propyl | |
| 4.33 | Br | H | n-Propyl | cyclopropyl | |
| 4.34 | H | Cl | n-Propyl | cyclopropyl | |
| 4.35 | H | Cl | n-Propyl | cyclopropyl | |
| 4.36 | Br | H | n-Propyl | n-Butyl | 120–121 |
| 4.37 | H | Cl | n-Propyl | n-Butyl | |
| 4.38 | H | Cl | n-Propyl | n-Butyl | |
| 4.39 | H | I | n-Propyl | n-Butyl | |
| 4.40 | Br | H | n-Propyl | i-Butyl | |
| 4.41 | H | Cl | n-Propyl | i-Butyl | |
| 4.42 | Br | H | n-Propyl | cyclopropyl-CH₂ | |

TABELLE 4-continued

A = Thienyl[3.2-d]

| Cmpd. No. | R₁ | R₂ | R₃ | R₄ | phys. data |
|---|---|---|---|---|---|
| 4.43 | H | Cl | n-Porpyl |  | |
| 4.44 | H | Cl | n-Propyl |  | |
| 4.45 | H | Cl | n-Propyl |  | |
| 4.46 | H | Cl | n-Propyl |  | |
| 4.47 | Br | H | n-Propyl | Cyclobutyl | |
| 4.48 | Br | H | n-Propyl | n-Pentyl | |
| 4.49 | H | Cl | n-Propyl | n-Pentyl | |
| 4.50 | H | Cl | n-Propyl | n-Pentyl | |
| 4.51 | Br | H | n-Propyl | Cyclopentyl | |
| 4.52 | Br | H | n-Propyl | n-Hexyl | |
| 4.53 | Br | H | n-Propyl | Cyclohexyl | |
| 4.54 | Br | H | n-Propyl | Phenyl | |
| 4.55 | Br | H | n-Propyl | 4-Chlorophenyl | |
| 4.55 | H | Cl | n-Propyl | 4-Chlorophenyl | |
| 4.56 | Br | H | n-Propyl | 4-Phenoxyphenyl | |
| 4.57 | Br | H | n-Butyl | Me | |
| 4.58 | H | Cl | n-Butyl | Et | |
| 4.59 | Br | H | n-Butyl | n-Propyl | |
| 4.60 | H | Cl | n-Butyl | n-Propyl | |
| 4.61 | H | Cl | n-Butyl | n-Propyl | |
| 4.62 | H | I | n-Butyl | n-Propyl | |
| 4.62 | Br | H | n-Butyl |  | |
| 4.63 | H | Cl | n-Butyl |  | |
| 4.64 | H | Cl | n-Butyl |  | |
| 4.65 | Br | H | n-Butyl | n-Butyl | |
| 4.66 | H | Cl | n-Butyl | n-Butyl | |
| 4.67 | H | Cl | n-Butyl | n-Butyl | |
| 4.68 | H | I | n-Butyl | n-Butyl | |
| 4.69 | Br | H | n-Butyl | i-Butyl | |
| 4.70 | H | Cl | n-Butyl | i-Butyl | |
| 4.71 | Br | H | n-Butyl |  | |
| 4.72 | H | Cl | n-Butyl |  | |
| 4.73 | H | Cl | n-Butyl |  | |
| 4.74 | Br | H | n-Butyl |  | |
| 4.75 | H | Cl | n-Butyl | 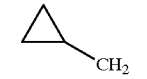 | |
| 4.76 | Br | H | n-Butyl | Cyclobutyl | |
| 4.77 | Br | H | n-Butyl | n-Pentyl | |
| 4.78 | H | Cl | n-Butyl | n-Pentyl | |
| 4.79 | H | Cl | n-Butyl | n-Pentyl | |
| 4.80 | Br | H | n-Butyl | Cyclopentyl | |
| 4.81 | Br | H | n-Butyl | n-Hexyl | |
| 4.82 | Br | H | n-Butyl | Cyclohexyl | |
| 4.83 | Br | H | n-Butyl | Phenyl | |
| 4.84 | Br | H | n-Butyl | 4-Chlorophenyl | |
| 4.85 | H | Cl | n-Butyl | 4-Chlorophenyl | |
| 4.86 | Br | H | n-Butyl | 4-Phenoxyphenyl | |
| 4.87 | Br | H | i-Butyl | n-Propyl | |
| 4.88 | H | Cl | i-Butyl | n-Propyl | |
| 4.89 | Br | H | i-Butyl | n-Butyl | |
| 4.90 | H | Cl | i-Butyl | n-Butyl | |
| 4.91 | Br | H | 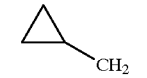 | n-Propyl | |
| 4.92 | H | Cl |  | n-Propyl | |
| 4.93 | Br | H |  | n-Propyl | |

TABELLE 4-continued

A = Thienyl[3.2-d]

| Cmpd. No. | R₁ | R₂ | R₃ | R₄ | phys. data |
|---|---|---|---|---|---|
| 4.94 | Br | H | cyclopropyl-CH₂ | n-Butyl | |
| 4.95 | Br | H | n-Pentyl | Me | |
| 4.96 | H | Cl | n-Pentyl | Et | |
| 4.97 | Br | H | n-Pentyl | n-Propyl | |
| 4.98 | Cl | H | n-Pentyl | n-Propyl | |
| 4.99 | H | Cl | n-Pentyl | n-Propyl | |
| 4.100 | H | I | n-Pentyl | n-Propyl | |
| 4.101 | Br | H | n-Pentyl | cyclopropyl | |
| 4.102 | H | Cl | n-Pentyl | cyclopropyl | |
| 4.103 | H | Cl | n-Pentyl | cyclopropyl | |
| 4.104 | Br | H | n-Pentyl | n-Butyl | |
| 4.105 | H | Cl | n-Pentyl | n-Butyl | |
| 4.106 | H | Cl | n-Pentyl | n-Butyl | |
| 4.107 | H | I | n-Pentyl | n-Butyl | |
| 4.108 | Br | H | n-Pentyl | i-Butyl | |
| 4.109 | H | Cl | n-Pentyl | i-Butyl | |
| 4.110 | Br | H | n-Pentyl | cyclopropyl-ethyl | |
| 4.111 | H | Cl | n-Pentyl | cyclopropyl-ethyl | |
| 4.112 | H | Cl | n-Pentyl | cyclopropyl-ethyl | |
| 4.113 | Br | H | n-Pentyl | methylcyclopropyl | |
| 4.114 | H | Cl | n-Pentyl | methylcyclopropyl | |
| 4.115 | Br | H | n-Pentyl | Cyclobutyl | |
| 4.116 | Br | H | n-Pentyl | n-Pentyl | |
| 4.117 | Cl | Cl | n-Pentyl | n-Pentyl | |
| 4.118 | H | Cl | n-Pentyl | n-Pentyl | |
| 4.119 | Br | H | n-Pentyl | Cyclopentyl | |
| 4.120 | Br | H | n-Pentyl | n-Hexyl | |
| 4.121 | Br | H | n-Pentyl | Cyclohexyl | |
| 4.122 | Br | H | n-Pentyl | Phenyl | |
| 4.123 | Br | H | n-Pentyl | 4-Chloro-phenyl | |
| 4.124 | H | Cl | n-Pentyl | 4-Chloro-phenyl | |
| 4.125 | Br | H | n-Pentyl | 4-Phenoxy-phenyl | |
| 4.126 | Br | H | OEt | Me | |
| 4.127 | Cl | H | OEt | Et | |
| 4.128 | Br | H | OEt | n-Propyl | |
| 4.129 | H | Cl | OEt | n-Propyl | |
| 4.130 | H | Cl | OEt | n-Propyl | |
| 4.131 | H | I | OEt | n-Propyl | |
| 4.132 | Br | H | OEt | cyclopropyl | |
| 4.133 | H | Cl | OEt | cyclopropyl | |
| 4.134 | H | Cl | OEt | cyclopropyl | |
| 4.135 | Br | H | OEt | n-Butyl | |
| 4.136 | H | Cl | OEt | n-Butyl | |
| 4.137 | H | Cl | OEt | n-Butyl | |
| 4.138 | H | I | OEt | n-Butyl | |
| 4.139 | Br | H | OEt | i-Butyl | |
| 4.140 | H | Cl | OEt | i-Butyl | |
| 4.141 | Br | H | OEt | cyclopropyl-ethyl | |
| 4.142 | H | Cl | OEt | cyclopropyl-ethyl | |
| 4.143 | H | Cl | OEt | cyclopropyl-ethyl | |
| 4.144 | Br | H | OEt | methylcyclopropyl | |
| 4.145 | H | Cl | OEt | methylcyclopropyl | |
| 4.146 | Br | H | OEt | Cyclobutyl | |

TABELLE 4-continued

A = Thienyl[3.2-d]

| Cmpd. No. | R₁ | R₂ | R₃ | R₄ | phys. data |
|---|---|---|---|---|---|
| 4.147 | Br | H | OEt | n-Pentyl | |
| 4.148 | H | Cl | OEt | n-Pentyl | |
| 4.149 | H | Cl | OEt | n-Pentyl | |
| 4.150 | Br | H | OEt | Cyclopentyl | |
| 4.151 | Br | H | OEt | n-Hexyl | |
| 4.152 | Br | H | OEt | Cyclohexyl | |
| 4.153 | Br | H | OEt | Phenyl | |
| 4.154 | Br | H | OEt | 4-Chloro-phenyl | |
| 4.155 | | Cl | OEt | 4-Chloro-phenyl | |
| 4.156 | Br | H | OEt | 4-Phenoxy-phenyl | |
| 4.157 | Br | H | O-n-Propyl | Me | |
| 4.158 | H | Cl | O-n-Propyl | Et | |
| 4.159 | Br | H | O-n-Propyl | n-Propyl | |
| 4.160 | H | Cl | O-n-Propyl | n-Propyl | |
| 4.161 | H | Cl | O-n-Propyl | n-Propyl | |
| 4.162 | H | I | O-n-Propyl | n-Propyl | |
| 4.163 | Br | H | O-n-Propyl |  | |
| 4.164 | H | Cl | O-n-Propyl |  | |
| 4.165 | H | Cl | O-n-Propyl |  | |
| 4.166 | Br | H | O-n-Propyl | n-Butyl | |
| 4.167 | H | Cl | O-n-Propyl | n-Butyl | |
| 4.168 | H | Cl | O-n-Propyl | n-Butyl | |
| 4.169 | H | H | O-n-Propyl | n-Butyl | |
| 4.170 | Br | H | O-n-Propyl | i-Butyl | |
| 4.171 | H | Cl | O-n-Propyl | i-Butyl | |
| 4.172 | Br | H | O-n-Propyl |  | |
| 4.173 | H | Cl | O-n-Propyl |  | |
| 4.174 | H | Cl | O-n-Propyl | 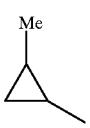 | |
| 4.175 | Br | H | O-n-Propyl |  | |
| 4.176 | H | Cl | O-n-Propyl | 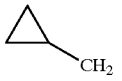 | |
| 4.177 | Br | H | O-n-Propyl | Cyclobutyl | |
| 4.178 | Br | H | O-n-Propyl | n-Pentyl | |
| 4.179 | H | Cl | O-n-Propyl | n-Pentyl | |
| 4.180 | H | Cl | O-n-Propyl | n-Pentyl | |
| 4.181 | Br | H | O-n-Propyl | Cyclopentyl | |
| 4.182 | Br | H | O-n-Propyl | n-Hexyl | |
| 4.183 | Br | H | O-n-Propyl | Cyclohexyl | |
| 4.184 | Br | H | O-n-Propyl | Phenyl | |
| 4.185 | Br | H | O-n-Propyl | 4-Chloro-phenyl | |
| 4.186 | H | Cl | O-n-Propyl | 4-Chloro-phenyl | |
| 4.187 | Br | H | O-n-Propyl | 4-Phenoxy-phenyl | |
| 4.188 | Br | H | Et | CH₂OMe | |
| 4.189 | H | Cl | Et | CH₂OMe | |
| 4.190 | Br | H | n-Propyl | CH₂OMe | |
| 4.191 | H | Cl | n-Propyl | CH₂OMe | |
| 4.192 | H | Cl | n-Propyl | CH₂OMe | |
| 4.193 | Br | H | n-Butyl | CH₂OMe | |
| 4.194 | H | Cl | n-Butyl | CH₂OMe | |
| 4.195 | Br | H | 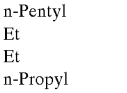 | CH₂OMe | |
| 4.195 | Br | H | n-Pentyl | CH₂OMe | |
| 4.196 | Br | H | Et | CH₂OEt | |
| 4.197 | H | Cl | Et | CH₂OEt | |
| 4.198 | Br | H | n-Propyl | CH₂OEt | |
| 4.199 | H | Cl | n-Propyl | CH₂OEt | |
| 4.200 | H | Cl | n-Propyl | CH₂OEt | |
| 4.201 | Br | H | n-Butyl | CH₂OEt | |
| 4.202 | H | Cl | n-Butyl | CH₂OEt | |
| 4.203 | Br | H | 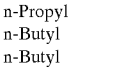 | CH₂OEt | |
| 4.204 | Br | H | n-Pentyl | CH₂OEt | |
| 4.205 | Br | H | n-Propyl | CH₂CN | |
| 4.206 | Br | H | n-Butyl | CH₂CN | |
| 4.207 | Br | H | n-Propyl | t-Butyl | |
| 4.208 | Br | H | n-Propyl | t-Butyl | |
| 4.209 | H | Cl | n-Propyl | CF₃ | |
| 4.210 | Br | H | n-Propyl | CF₃ | |
| 4.211 | H | Cl | n-Butyl | CF₃ | |
| 4.212 | Br | H | n-Butyl | CF₃ | |
| 4.213 | Cl | Cl | n-Propyl | n-Propyl | |
| 4.214 | Cl | Cl | n-Propyl | n-Butyl | |
| 4.215 | Br | Br | n-Propyl | n-Butyl | |
| 4.216 | Br | Br | n-Butyl | n-Butyl | |

TABELLE 5

A = Thiazolyl

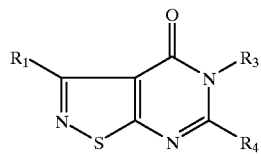

| Cmpd. No. | R₁ | R₃ | R₄ | phys. data |
|---|---|---|---|---|
| 5.1 | H | Et | n-Propyl | |
| 5.2 | H | n-Propyl | n-Propyl | |
| 5.3 | H | n-Propyl | n-Butyl | |
| 5.4 | H | n-Butyl | n-Butyl | |
| 5.5 | Me | n-Propyl | n-Propyl | |
| 5.6 | Me | n-Propyl | n-Butyl | |
| 5.7 | Me | n-Butyl | n-Butyl | |
| 5.8 | H | n-Propyl | Phenyl | |

TABELLE 6

A = Phenyl

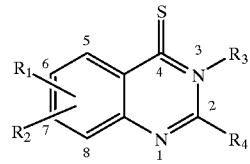

| cmpd. No. | R₁ | R₂ | R₃ | R₄ | phys. data m.p. ° C. |
|---|---|---|---|---|---|
| 6.1 | 6-Br | H | Me | Me | |
| 6.2 | 6-Cl | H | Me | Et | |
| 6.3 | 6-Br | H | Me | n-Propyl | |
| 6.4 | 6-Cl | H | Me | n-Propyl | |
| 6.5 | H | 7-Cl | Me | n-Propyl | |
| 6.6 | 6-Br | H | Me | n-Butyl | |
| 6.7 | 6-Cl | H | Me | n-Butyl | |
| 6.8 | H | 7-Cl | Me | n-Butyl | |
| 6.9 | 6-Br | H | Me | i-Butyl | |
| 6.10 | 6-Cl | H | Me | i-Butyl | |
| 6.11 | 6-Br | H | Me | n-Pentyl | |
| 6.12 | 6-Br | H | Me | cyclopropyl-CH₂ | |
| 6.13 | 6-Cl | H | Me | cyclopropyl-CH₂ | |
| 6.14 | 6-Br | H | Et | Me | |
| 6.15 | 6-Cl | H | Et | Et | |
| 6.16 | 6-Br | H | Et | n-Propyl | |
| 6.17 | 6-Cl | H | Et | n-Propyl | |
| 6.18 | H | 7-Cl | Et | n-Propyl | |
| 6.19 | 6-Br | H | Et | n-Butyl | |
| 6.20 | 6-Cl | H | Et | n-Butyl | |
| 6.21 | H | 7-Cl | Et | n-Butyl | |
| 6.22 | 6-Br | H | Et | i-Butyl | |
| 6.23 | 6-Cl | H | Et | i-Butyl | |
| 6.24 | 6-Br | H | Et | n-Pentyl | |

TABELLE 6-continued

A = Phenyl

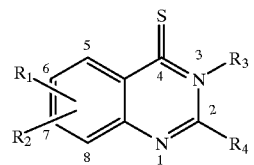

| cmpd. No. | R₁ | R₂ | R₃ | R₄ | phys. data m.p. ° C. |
|---|---|---|---|---|---|
| 6.25 | 6-Br | H | Et | cyclopropyl-CH₂ | |
| 6.26 | 6-Cl | H | Et | cyclopropyl-CH₂ | |
| 6.27 | 6-Br | H | n-Propyl | Me | |
| 6.28 | 6-Cl | H | n-Propyl | Et | |
| 6.29 | 6-Br | H | n-Propyl | n-Propyl | Oil, ¹H-NMR |
| 6.30 | 6-Cl | H | n-Propyl | n-Propyl | |
| 6.31 | H | 7-Cl | n-Propyl | n-Propyl | |
| 6.32 | H | 7-I | n-Propyl | n-Propyl | |
| 6.33 | 6-Br | H | n-Propyl | cyclopropyl | |
| 6.34 | 6-Cl | H | n-Propyl | cyclopropyl | |
| 6.35 | H | 7-Cl | n-Propyl | cyclopropyl | |
| 6.36 | 6-Br | H | n-Propyl | n-Butyl | |
| 6.37 | 6-Cl | H | n-Propyl | n-Butyl | |
| 6.38 | H | 7-Cl | n-Propyl | n-Butyl | |
| 6.39 | H | 7-I | n-Propyl | n-Butyl | |
| 6.40 | 6-Br | H | n-Propyl | i-Butyl | |
| 6.41 | 6-Cl | H | n-Propyl | i-Butyl | |
| 6.42 | 6-Br | H | n-Propyl | cyclopropyl-CH₂ | |
| 6.43 | 6-Cl | H | n-Propyl | cyclopropyl-CH₂ | |
| 6.44 | H | 7-Cl | n-Propyl | cyclopropyl-CH₂ | |
| 6.45 | 6-Br | H | n-Propyl | (2-methylcyclopropyl)-CH₂ | |

TABELLE 6-continued

A = Phenyl

| cmpd. No. | R$_1$ | R$_2$ | R$_3$ | R$_4$ | phys. data m.p. °C. |
|---|---|---|---|---|---|
| 6.46 | 6-Cl | H | n-Prpyl | cyclopropylmethyl (Me-cyclopropyl-CH$_2$) | |
| 6.47 | 6-Br | H | n-Propyl | Cyclobutyl | |
| 6.48 | 6-Br | H | n-Propyl | n-Pentyl | |
| 6.49 | 6-Cl | H | n-Propyl | n-Pentyl | |
| 6.50 | H | 7-Cl | n-Propyl | n-Pentyl | |
| 6.51 | 6-Br | H | n-Propyl | Cyclopentyl | |
| 6.52 | 6-Br | H | n-Propyl | n-Hexyl | |
| 6.53 | 6-Br | H | n-Propyl | Cyclohexyl | |
| 6.54 | 6-Br | H | n-Propyl | Phenyl | |
| 6.55 | 6-Br | H | n-Propyl | 4-Chloro-phenyl | |
| 6.56 | 6-Cl | H | n-Propyl | 4-Chloro-phenyl | |
| 6.57 | 6-Br | H | n-Propyl | 4-Phenoxy-phenyl | |
| 6.58 | 6-Br | H | n-Butyl | Me | |
| 6.59 | 6-Cl | H | n-Butyl | Et | |
| 6.60 | 6-Br | H | n-Butyl | n-Propyl | |
| 6.61 | 6-Cl | H | n-Butyl | n-Propyl | |
| 6.62 | H | 7-Cl | n-Butyl | n-Propyl | |
| 6.63 | H | 7-I | n-Butyl | n-Propyl | |
| 6.64 | 6-Br | H | n-Butyl | cyclopropyl | |
| 6.65 | 6-Cl | H | n-Butyl | cyclopropyl | |
| 6.66 | H | 7-Cl | n-Butyl | cyclopropyl | |
| 6.67 | 6-Br | H | n-Butyl | n-Butyl | |
| 6.68 | 6-Cl | H | n-Butyl | n-Butyl | |
| 6.69 | H | 7-Cl | n-Butyl | n-Butyl | |
| 6.70 | H | 7-I | n-Butyl | n-Butyl | |
| 6.71 | 6-Br | H | n-Butyl | i-Butyl | |
| 6.72 | 6-Cl | H | n-Butyl | i-Butyl | |
| 6.73 | 6-Br | H | n-Butyl | methylcyclopropyl | |
| 6.74 | 6-Cl | H | n-Butyl | methylcyclopropyl | |
| 6.75 | H | 7-Cl | n-Butyl | methylcyclopropyl | |
| 6.76 | 6-Br | H | n-Butyl | (2-methylcyclopropyl)methyl | |
| 6.77 | 6-Cl | H | n-Butyl | (2-methylcyclopropyl)methyl | |
| 6.78 | 6-Br | H | n-Butyl | Cyclobutyl | |
| 6.79 | 6-Br | H | n-Butyl | n-Pentyl | |
| 6.80 | 6-Cl | H | n-Butyl | n-Pentyl | |
| 6.81 | H | 7-Cl | n-Butyl | n-Pentyl | |
| 6.82 | 6-Br | H | n-Butyl | Cyclopentyl | |
| 6.83 | 6-Br | H | n-Butyl | n-Hexyl | |
| 6.84 | 6-Br | H | n-Butyl | Cyclohexyl | |
| 6.85 | 6-Br | H | n-Butyl | Phenyl | |
| 6.86 | 6-Br | H | n-Butyl | 4-Chloro-phenyl | |
| 6.87 | 6-Cl | H | n-Butyl | 4-Chloro-phenyl | |
| 6.88 | 6-Br | H | n-Butyl | 4-Phenoxy-phenyl | |
| 6.89 | 6-Br | H | i-Butyl | n-Propyl | |
| 6.90 | 6-Cl | H | i-Butyl | n-Propyl | |
| 6.91 | 6-Br | H | i-Butyl | n-Butyl | |
| 6.92 | 6-Cl | H | i-Butyl | n-Butyl | |
| 6.93 | 6-Br | H | cyclopropylmethyl | n-Propyl | |
| 6.94 | 6-Cl | H | cyclopropylmethyl | n-Propyl | |
| 6.95 | 6-Br | H | (2-methylcyclopropyl)methyl | n-Propyl | |
| 6.96 | 6-Br | H | (2-methylcyclopropyl)methyl | n-Butyl | |
| 6.97 | 6-Br | H | n-Pentyl | Me | |
| 6.98 | 6-Cl | H | n-Pentyl | Et | |
| 6.99 | 6-Br | H | n-Pentyl | n-Propyl | |
| 6.100 | 6-Cl | H | n-Pentyl | n-Propyl | |

TABELLE 6-continued

A = Phenyl

| cmpd. No. | R₁ | R₂ | R₃ | R₄ | phys. data m.p. °C. |
|---|---|---|---|---|---|
| 6.101 | H | 7-Cl | n-Pentyl | n-Propyl | |
| 6.102 | H | 7-I | n-Pentyl | n-Propyl | |
| 6.103 | 6-Br | H | n-Pentyl |  | |
| 6.104 | 6-Cl | H | n-Pentyl |  | |
| 6.105 | H | 7-Cl | n-Pentyl |  | |
| 6.106 | 6-Br | H | n-Pentyl | n-Butyl | |
| 6.107 | 6-Cl | H | n-Pentyl | n-Butyl | |
| 6.108 | H | 7-Cl | n-Pentyl | n-Butyl | |
| 6.109 | H | 7-I | n-Pentyl | n-Butyl | |
| 6.110 | 6-Br | H | n-Pentyl | i-Butyl | |
| 6.111 | 6-Cl | H | n-Pentyl | i-Butyl | |
| 6.112 | 6-Br | H | n-Pentyl |  | |
| 6.113 | 6-Cl | H | n-Pentyl |  | |
| 6.114 | H | 7-Cl | n-Pentyl | 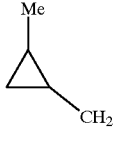 | |
| 6.115 | 6-Br | H | n-Pentyl | 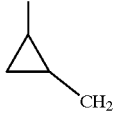 | |
| 6.116 | 6-Cl | H | n-Pentyl |  | |
| 6.117 | 6-Br | H | n-Pentyl | Cyclobutyl | |
| 6.118 | 6-Br | H | n-Pentyl | n-Pentyl | |
| 6.119 | 6-Cl | H | n-Pentyl | n-Pentyl | |
| 6.120 | H | 7-Cl | n-Pentyl | n-Pentyl | |
| 6.121 | 6-Br | H | n-Pentyl | Cyclopentyl | |
| 6.122 | 6-Br | H | n-Pentyl | n-Hexyl | |
| 6.123 | 6-Br | H | n-Pentyl | Cyclohexyl | |
| 6.124 | 6-Br | H | n-Pentyl | Phenyl | |
| 6.125 | 6-Br | H | n-Pentyl | 4-Chloro-phenyl | |
| 6.126 | 6-Cl | H | n-Pentyl | 4-Chloro-phenyl | |
| 6.127 | 6-Br | H | n-Pentyl | 4-Phenoxy- | |
| 6.128 | 6-Br | H | OEt | phenyl | |
| 6.129 | 6-Cl | H | OEt | Me | |
| 6.129 | 6-Cl | H | OEt | Et | |
| 6.130 | 6-Br | H | OEt | n-Propyl | |
| 6.131 | 6-Cl | H | OEt | n-Propyl | |
| 6.132 | H | 7-Cl | OEt | n-Propyl | |
| 6.133 | H | 7-I | OEt | n-Propyl | |
| 6.134 | 6-Br | H | OEt |  | |
| 6.135 | 6-Cl | H | OEt |  | |
| 6.136 | H | 7-Cl | OEt |  | |
| 6.137 | 6-Br | H | OEt | n-Butyl | |
| 6.138 | 6-Cl | H | OEt | n-Butyl | |
| 6.139 | H | 7-Cl | OEt | n-Butyl | |
| 6.140 | H | 7-I | OEt | n-Butyl | |
| 6.141 | 6-Br | H | OEt | i-Butyl | |
| 6.142 | 6-Cl | H | OEt | i-Butyl | |
| 6.143 | 6-Br | H | OEt |  | |
| 6.144 | 6-Cl | H | OEt |  | |
| 6.145 | H | 7-Cl | OEt |  | |
| 6.146 | 6-Br | H | OEt | 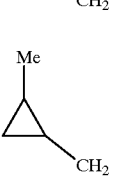 | |
| 6.147 | 6-Cl | H | OEt | | |
| 6.148 | 6-Br | H | OEt | Cyclobutyl | |
| 6.149 | 6-Br | H | OEt | n-Pentyl | |
| 6.150 | 6-Cl | H | OEt | n-Pentyl | |
| 6.151 | H | 7-Cl | OEt | n-Pentyl | |
| 6.152 | 6-Br | H | OEt | Cyclopentyl | |
| 6.153 | 6-Br | H | OEt | n-Hexyl | |
| 6.154 | 6-Br | H | OEt | Cyclohexyl | |
| 6.155 | 6-Br | H | OEt | Phenyl | |

TABELLE 6-continued

A = Phenyl

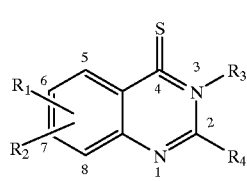

| cmpd. No. | R₁ | R₂ | R₃ | R₄ | phys. data m.p. ° C. |
|---|---|---|---|---|---|
| 6.156 | 6-Br | H | OEt | 4-Chlorophenyl | |
| 6.157 | 6-Cl | H | OEt | 4-Chlorophenyl | |
| 6.158 | 6-Br | H | OEt | 4-Phenoxyphenyl | |
| 6.159 | 6-Br | H | O-n-Propyl | Me | |
| 6.160 | 6-Cl | H | O-n-Propyl | Et | |
| 6.161 | 6-Br | H | O-n-Propyl | n-Propyl | |
| 6.162 | 6-Cl | H | O-n-Propyl | n-Propyl | |
| 6.163 | H | 7-Cl | O-n-Propyl | n-Propyl | |
| 6.164 | H | 7-I | O-n-Propyl | n-Propyl | |
| 6.165 | 6-Br | H | O-n-Propyl | cyclopropyl | |
| 6.166 | 6-Cl | H | O-n-Propyl | cyclopropyl | |
| 6.167 | H | 7-Cl | O-n-Propyl | cyclopropyl | |
| 6.168 | 6-Br | H | O-n-Propyl | n-Butyl | |
| 6.169 | 6-Cl | H | O-n-Propyl | n-Butyl | |
| 6.170 | H | 7-Cl | O-n-Propyl | n-Butyl | |
| 6.171 | H | 7-I | O-n-Propyl | n-Butyl | |
| 6.172 | 6-Br | H | O-n-Propyl | i-Butyl | |
| 6.173 | 6-Cl | H | O-n-Propyl | i-Butyl | |
| 6.174 | 6-Br | H | O-n-Propyl | cyclopropylmethyl | |
| 6.175 | 6-Cl | H | O-n-Propyl | cyclopropylmethyl | |
| 6.176 | H | 7-Cl | O-n-Propyl | cyclopropylmethyl | |
| 6.177 | 6-Br | H | O-n-Propyl | (2-Me-cyclopropyl)methyl | |
| 6.178 | 6-Cl | H | O-n-Propyl | (2-Me-cyclopropyl)methyl | |
| 6.179 | 6-Br | H | O-n-Propyl | Cyclobutyl | |
| 6.180 | 6-Br | H | O-n-Propyl | n-Pentyl | |
| 6.181 | 6-Cl | H | O-n-Propyl | n-Pentyl | |
| 6.182 | H | 7-Cl | O-n-Propyl | n-Pentyl | |
| 6.183 | 6-Br | H | O-n-Propyl | Cyclopentyl | |
| 6.184 | 6-Br | H | O-n-Prpyl | n-Hexyl | |
| 6.185 | 6-Br | H | O-n-Prpyl | Cyclohexyl | |
| 6.186 | 6-Br | H | O-n-Prpyl | Phenyl | |
| 6.187 | 6-Br | H | O-n-Prpyl | 4-Chlorophenyl | |
| 6.188 | 6-Cl | H | O-n-Prpyl | 4-Chlorophenyl | |
| 6.189 | 6-Br | H | O-n-Prpyl | 4-Phenoxyphenyl | |
| 6.190 | 6-Br | H | Et | CH₂OMe | |
| 6.191 | 6-Cl | H | Et | CH₂OMe | |
| 6.192 | 6-Br | H | n-Prpyl | CH₂OMe | |
| 6.193 | 6-Cl | H | n-Prpyl | CH₂OMe | |
| 6.194 | H | 7-Cl | n-Prpyl | CH₂OMe | |
| 6.195 | 6-Br | H | n-Butyl | CH₂OMe | |
| 6.196 | 6-Cl | H | n-Butyl | CH₂OMe | |
| 6.197 | 6-Br | H | cyclopropylmethyl | CH₂OMe | |
| 6.198 | 6-Br | H | n-Pentyl | CH₂OMe | |
| 6.199 | 6-Br | H | Et | CH₂OEt | |
| 6.200 | 6-Cl | H | Et | CH₂OEt | |
| 6.201 | 6-Br | H | n-Propyl | CH₂OEt | |
| 6.202 | 6-Cl | H | n-Propyl | CH₂OEt | |
| 6.203 | H | 7-Cl | n-Propyl | CH₂OEt | |
| 6.204 | 6-Br | H | n-Butyl | CH₂OEt | |
| 6.205 | 6-Cl | H | n-Butyl | CH₂OEt | |
| 6.206 | 6-Br | H | cyclopropylmethyl | CH₂OEt | |
| 6.207 | 6-Br | H | n-Pentyl | CH₂OEt | |
| 6.208 | 6-Br | H | n-Propyl | CH₂CN | |
| 6.209 | 6-Br | H | n-Butyl | CH₂CN | |
| 6.210 | 6-Br | H | n-Propyl | t-Butyl | |
| 6.211 | 6-Br | H | n-Propyl | t-Butyl | |
| 6.212 | 6-Cl | H | n-Propyl | CF₃ | |
| 6.213 | 6-Br | H | n-Propyl | CF₃ | |
| 6.214 | 6-Br | H | n-Butyl | CF₃ | |

TABELLE 7

A = Thienyl[2.3-d]

| cmpd. No. | R₁ | R₂ | R₃ | R₄ | phys. data m.p. °C |
|---|---|---|---|---|---|
| 7.1 | Br | H | Me | Me | |
| 7.2 | Cl | H | Me | Et | |
| 7.3 | Br | H | Me | n-Propyl | |
| 7.4 | Cl | H | Me | n-Propyl | |
| 7.5 | Br | H | Me | n-Butyl | |
| 7.6 | Cl | H | Me | n-Butyl | 113–114 |
| 7.7 | Br | H | Me | i-Butyl | |
| 7.8 | Cl | H | Me | i-Butyl | |
| 7.9 | Br | H | Me | n-Pentyl | |
| 7.10 | Br | H | Me | cyclopropyl-CH₂ | |
| 7.11 | Cl | H | Me | cyclopropyl-CH₂ | |
| 7.12 | Br | H | Et | Me | |
| 7.13 | Cl | H | Et | Et | |
| 7.14 | Br | H | Et | n-Propyl | |
| 7.15 | Cl | H | Et | n-Propyl | |
| 7.16 | Br | H | Et | n-Butyl | |
| 7.17 | Cl | H | Et | n-Butyl | |
| 7.18 | Br | H | Et | i-Butyl | |
| 7.19 | Cl | H | Et | i-Butyl | |
| 7.20 | Br | H | Et | n-Pentyl | |
| 7.21 | Br | H | Et | cyclopropyl-CH₂ | |
| 7.22 | Cl | H | Et | cyclopropyl-CH₂ | |
| 7.23 | Br | H | n-Propyl | Me | |
| 7.24 | Cl | H | n-Propyl | Et | |
| 7.25 | Br | H | n-Propyl | n-Propyl | |
| 7.26 | Cl | H | n-Propyl | n-Propyl | |
| 7.27 | I | H | n-Propyl | n-Propyl | |
| 7.28 | Br | H | n-Propyl | cyclopropyl | |
| 7.29 | Cl | H | n-Propyl | cyclopropyl | |
| 7.30 | Br | H | n-Propyl | n-Butyl | |
| 7.31 | Cl | H | n-Propyl | n-Butyl | Oil, ¹H-NMR |
| 7.32 | I | H | n-Propyl | n-Butyl | |
| 7.33 | Br | H | n-Propyl | i-Butyl | |
| 7.34 | Cl | H | n-Propyl | i-Butyl | 57–60 |
| 7.35 | Br | H | n-Propyl | methylcyclopropyl | |
| 7.36 | Cl | H | n-Propyl | methylcyclopropyl | |
| 7.37 | Br | H | n-Propyl | 2-methylcyclopropyl | |
| 7.38 | Cl | H | n-Propyl | 2-methylcyclopropyl | |
| 7.39 | Br | H | n-Propyl | Cyclobutyl | |
| 7.40 | Br | H | n-Propyl | n-Pentyl | |
| 7.41 | Cl | H | n-Propyl | n-Pentyl | |
| 7.42 | Br | H | n-Propyl | Cyclopentyl | |
| 7.43 | Br | H | n-Propyl | n-Hexyl | |
| 7.44 | Br | H | n-Propyl | Cyclohexyl | |
| 7.45 | Br | H | n-Propyl | Phenyl | |
| 7.46 | Br | H | n-Propyl | 4-Chloro-phenyl | |
| 7.47 | Cl | H | n-Propyl | 4-Chloro-phenyl | |
| 7.48 | Br | H | n-Propyl | 4-Phenoxy-phenyl | |
| 7.49 | Br | H | n-Butyl | Me | |
| 7.50 | Cl | H | n-Butyl | Et | |
| 7.51 | Br | H | n-Butyl | n-Propyl | |
| 7.52 | Cl | H | n-Butyl | n-Propyl | |
| 7.53 | I | H | n-Butyl | n-Propyl | |
| 7.54 | I | H | n-Butyl | n-Propyl | |
| 7.55 | Br | H | n-Butyl | cyclopropyl | |
| 7.56 | Cl | H | n-Butyl | cyclopropyl | |
| 7.57 | I | H | n-Butyl | cyclopropyl | |
| 7.58 | Br | H | n-Butyl | n-Butyl | |
| 7.59 | Cl | H | n-Butyl | n-Butyl | |
| 7.60 | I | H | n-Butyl | n-Butyl | |
| 7.61 | Br | H | n-Butyl | i-Butyl | |
| 7.62 | Cl | H | n-Butyl | i-Butyl | |
| 7.63 | Br | H | n-Butyl | methylcyclopropyl | |

TABELLE 7-continued

A = Thienyl[2.3-d]

Structure: thieno[2,3-d]pyrimidine-4-thione with R₁ at position 6, R₂ at position 5, R₃ at position 3 (N), R₄ at position 2.

| cmpd. No. | R₁ | R₂ | R₃ | R₄ | phys. data m.p. °C. |
|---|---|---|---|---|---|
| 7.64 | Cl | H | n-Butyl | cyclopropyl | |
| 7.65 | I | H | n-Butyl | cyclopropyl | |
| 7.66 | Br | H | n-Butyl | 2-methylcyclopropyl | |
| 7.67 | Cl | H | n-Butyl | 2-methylcyclopropyl | |
| 7.68 | Br | H | n-Butyl | Cyclobutyl | |
| 7.69 | Br | H | n-Butyl | n-Pentyl | |
| 7.70 | Cl | H | n-Butyl | n-Pentyl | |
| 7.71 | Br | H | n-Butyl | Cyclopentyl | |
| 7.72 | Br | H | n-Butyl | n-Hexyl | |
| 7.73 | Br | H | n-Butyl | Cyclohexyl | |
| 7.74 | Cl | H | n-Butyl | Phenyl | |
| 7.75 | Br | H | n-Butyl | 4-Chloro-phenyl | |
| 7.76 | Cl | H | n-Butyl | 4-Chloro-phenyl | |
| 7.77 | Br | H | n-Butyl | 4-Phenoxy-phenyl | |
| 7.78 | Br | H | i-Butyl | n-Propyl | |
| 7.79 | Cl | H | i-Butyl | n-Propyl | |
| 7.80 | Br | H | i-Butyl | n-Butyl | |
| 7.81 | Cl | H | i-Butyl | n-Butyl | |
| 7.82 | Br | H | cyclopropyl-CH₂ | n-Propyl | |
| 7.83 | Cl | H | cyclopropyl-CH₂ | n-Propyl | |
| 7.84 | Cl | H | (2-methylcyclopropyl)-CH₂ | n-Propyl | |
| 7.85 | Br | H | (2-methylcyclopropyl)-CH₂ | n-Butyl | |
| 7.86 | Br | H | n-Pentyl | Me | |
| 7.87 | Cl | H | n-Pentyl | Et | |
| 7.88 | Br | H | n-Pentyl | n-Propyl | |
| 7.89 | Cl | H | n-Pentyl | n-Propyl | |
| 7.90 | Br | H | n-Pentyl | cyclopropyl | |
| 7.91 | Cl | H | n-Pentyl | cyclopropyl | |
| 7.92 | Br | H | n-Pentyl | n-Butyl | |
| 7.93 | Cl | H | n-Pentyl | n-Butyl | |
| 7.94 | I | H | n-Pentyl | n-Butyl | |
| 7.95 | Br | H | n-Pentyl | i-Butyl | |
| 7.96 | Cl | H | n-Pentyl | i-Butyl | |
| 7.97 | Br | H | n-Pentyl | cyclopropyl | |
| 7.98 | Cl | H | n-Pentyl | cyclopropyl | |
| 7.99 | Br | H | n-Pentyl | 2-methylcyclopropyl | |
| 7.100 | Cl | H | n-Pentyl | 2-methylcyclopropyl | |
| 7.101 | Cl | H | n-Pentyl | Cyclobutyl | |
| 7.102 | Br | H | n-Pentyl | n-Pentyl | |
| 7.103 | Cl | H | n-Pentyl | n-Pentyl | |
| 7.104 | Cl | H | n-Pentyl | Cyclopentyl | |
| 7.105 | Br | H | n-Pentyl | n-Hexyl | |
| 7.106 | Cl | H | n-Pentyl | Cyclohexyl | |
| 7.107 | Br | H | n-Pentyl | Phenyl | |
| 7.108 | Br | H | n-Pentyl | 4-Chloro-phenyl | |
| 7.109 | Cl | H | n-Pentyl | 4-Chloro-phenyl | |
| 7.110 | Br | H | n-Pentyl | 4-Phenoxy-phenyl | |
| 7.111 | Br | H | OEt | Me | |

TABELLE 7-continued

A = Thienyl[2.3-d]

| cmpd. No. | R₁ | R₂ | R₃ | R₄ | phys. data m.p. ° C. |
|---|---|---|---|---|---|
| 7.112 | Cl | H | OEt | Et | |
| 7.113 | Br | H | OEt | n-Propyl | |
| 7.114 | Cl | H | OEt | n-Propyl | |
| 7.115 | Br | H | OEt | cyclopropyl | |
| 7.116 | Cl | H | OEt | cyclopropyl | |
| 7.117 | Br | H | OEt | n-Butyl | |
| 7.118 | Cl | H | OEt | n-Butyl | |
| 7.119 | I | H | OEt | n-Butyl | |
| 7.120 | Br | H | OEt | i-Butyl | |
| 7.121 | Cl | H | OEt | i-Butyl | |
| 7.122 | Br | H | OEt | cyclopropyl-CH | |
| 7.123 | Cl | H | OEt | cyclopropyl-CH | |
| 7.124 | Br | H | OEt | Me-cyclopropyl | |
| 7.125 | Cl | H | OEt | Me-cyclopropyl | |
| 7.126 | Br | H | OEt | Cyclobutyl | |
| 7.127 | Br | H | OEt | n-Pentyl | |
| 7.128 | Cl | H | OEt | n-Pentyl | |
| 7.129 | Br | H | OEt | Cyclopentyl | |
| 7.130 | Br | H | OEt | n-Hexyl | |
| 7.131 | Br | H | OEt | Cyclohexyl | |
| 7.132 | Br | H | OEt | Phenyl | |
| 7.133 | Br | H | OEt | 4-Chloro-phenyl | |
| 7.134 | Cl | H | OEt | 4-Chloro-phenyl | |
| 7.135 | Cl | H | OEt | 4-Phenoxy-phenyl | |
| 7.136 | Br | H | O-n-Propyl | Me | |
| 7.137 | Cl | H | O-n-Propyl | Et | |
| 7.138 | Br | H | O-n-Propyl | n-Propyl | |
| 7.139 | Cl | H | O-n-Propyl | n-Propyl | |
| 7.140 | Br | H | O-n-Propyl | cyclopropyl | |
| 7.141 | Cl | H | O-n-Propyl | cyclopropyl | |
| 7.142 | Br | H | O-n-Propyl | n-Butyl | |
| 7.143 | Cl | H | O-n-Propyl | n-Butyl | |
| 7.144 | Br | H | O-n-Propyl | i-Butyl | |
| 7.145 | Cl | H | O-n-Propyl | i-Butyl | |
| 7.146 | Br | H | O-n-Propyl | cyclopropyl-CH | |
| 7.147 | Cl | H | O-n-Propyl | cyclopropyl-CH | |
| 7.148 | Br | H | O-n-Propyl | Me-cyclopropyl | |
| 7.149 | Cl | H | O-n-Propyl | Me-cyclopropyl | |
| 7.150 | Br | H | O-n-Propyl | Cyclobutyl | |
| 7.151 | Br | H | O-n-Propyl | n-Pentyl | |
| 7.152 | Cl | H | O-n-Propyl | n-Pentyl | |
| 7.153 | Br | H | O-n-Propyl | Cyclopentyl | |
| 7.154 | Cl | H | O-n-Propyl | n-Hexyl | |
| 7.155 | Br | H | O-n-Propyl | Cyclohexyl | |
| 7.156 | Cl | H | O-n-Propyl | Phenyl | |
| 7.157 | Br | H | O-n-Propyl | 4-Chloro-phenyl | |
| 7.158 | Cl | H | O-n-Propyl | 4-Chloro-phenyl | |
| 7.159 | Br | H | O-n-Propyl | 4-Phenoxy-phenyl | |
| 7.160 | Br | H | Et | CH₂OMe | |
| 7.161 | Cl | H | Et | CH₂OMe | |
| 7.162 | Br | H | n-Propyl | CH₂OMe | |
| 7.163 | Cl | H | n-Propyl | CH₂OMe | |
| 7.164 | Br | H | n-Butyl | CH₂OMe | |
| 7.165 | Cl | H | n-Butyl | CH₂OMe | |
| 7.166 | Br | H | cyclopropyl-CH₂ | CH₂OMe | |
| 7.167 | Br | H | n-Pentyl | CH₂OMe | |
| 7.168 | Br | H | Et | CH₂OEt | |
| 7.169 | Cl | H | Et | CH₂OEt | |
| 7.170 | Br | H | n-Propyl | CH₂OEt | |
| 7.171 | Cl | H | n-Propyl | CH₂OEt | |
| 7.172 | Br | H | n-Butyl | CH₂OEt | |

TABELLE 7-continued

A = Thienyl[2,3-d]

$$R_2 \underset{5}{\overset{S}{\underset{6}{\bigcirc}}} \underset{4}{\overset{3}{\underset{S}{\bigcirc}}} \underset{1}{\overset{R_3}{\underset{N}{\bigcirc}}} R_4$$

| cmpd. No. | $R_1$ | $R_2$ | $R_3$ | $R_4$ | phys. data m.p. °C. |
|---|---|---|---|---|---|
| 7.173 | Cl | H | n-Butyl | $CH_2OEt$ | |
| 7.174 | Br | H | △–$CH_2$ | $CH_2OEt$ | |
| 7.175 | Br | H | n-Pentyl | $CH_2OEt$ | |
| 7.176 | Br | H | n-Propyl | $CH_2CN$ | |
| 7.177 | Cl | H | n-Butyl | $CH_2CN$ | |
| 7.178 | Br | H | n-Propyl | t-Butyl | |
| 7.179 | Cl | H | n-Propyl | t-Butyl | |
| 7.180 | Br | H | n-Propyl | $CF_3$ | |
| 7.181 | Cl | H | n-Butyl | $CF_3$ | |
| 7.182 | Cl | H | n-Pentyl | $CF_3$ | |
| 7.183 | Cl | Cl | n-Propyl | n-Propyl | |
| 7.184 | Cl | Cl | n-Propyl | n-Butyl | |
| 7.185 | Br | Br | n-Propyl | n-Butyl | |
| 7.186 | Br | Br | n-Butyl | n-Butyl | |

Examples for specific formulations-combination are as disclosed e.g. in WO 97/33890, e.g. for wettable powders, emulsifiable concentrates, dusts, extruder granules, coated granules, solutions and suspension concentrates.

BIOLOGICAL EXAMPLES

Fungicidal Actions

Example B-1
Action Against *Colletotrichum lagenarium* on Cucumbers

After a growth period of 2 weeks, cucumber plants are sprayed with an aqueous spray mixture (concentration 0.002%) prepared from a wettable powder formulation of the test compound and infected 2 days later with a spore suspension ($1.5 \times 10^5$ spores/ml) of the fungus and incubated for 36 hours at 23° C. and high humidity. Incubation is then continued at normal humidity and c. 22° C. Evaluation of the fungal infestation is made 8 days after infection.

The compounds of the Tables 1–7 show good to excellent activity, preferably the compounds 1.36, 2.30, 3.1, 3.6, 3.8, 3.15, 3.17, 3.26, 3.30, 3.31, 3.47, 3.52, 3.56, 3.58, 3.59, 3.79, 3.117, 3.118, 3.163, 3.171, 4.36, 6.29, 7.6, 7.31 and 7.34.

Example B-2
Residual-Drotective Action Against *Venturia inaequalis* on Apples Apple cuttings with fresh shoots 10 to 20 cm long are sprayed to drip point with a spray mixture (0.02% a.i.) prepared from a wettable powder formulation of the test compound. The plants are infected 24 hours later with a conidia suspension of the fungus. The plants are then incubated for 5 days at 90 to 100% relative humidity and stood in a greenhouse for a further 10 days at 20 to 24° C. Evaluation of the fungal infestation is made 12 days after infection.

Compounds of Tables 1–7 show good activity, preferably the compounds 1.36, 2.30, 3.1, 3.6, 3.8, 3.15, 3.17, 3.26, 3.30, 3.31, 3.34, 3.36, 3.47, 3.52, 3.56, 3.58, 3.59, 3.79, 3.117, 3.118, 3.163, 3.171, 4.36, 6.29, 7.6, 7.31 and 7.34.

Example B-3
Action Against *Erysiphe graminis* on Barley
a) Residual-Drotective Action Barley plants about 8 cm in height are sprayed to drip point with a spray mixture (0.02% a.i.) prepared from a wettable powder formulation of the test compound, and the treated plants are dusted with conidia of the fungus 3 to 4 hours later. The infected plants are stood in a greenhouse at 22° C. Evaluation of the fungal infection is made 12 days after infection.

b) Systemic Action

Barley plants about 8 cm in height are drenched with an aqueous spray mixture (0.002% a.i., based on the volume of the soil) prepared from a wettable powder formulation of the test compound. Care is taken that the spray mixture does not come into contact with the growing parts of the plants. The treated plants are dusted 48 hours later with conidia of the fungus. The infected plants are then stood in a greenhouse at 22° C. Evaluation of the fungal infestation is made 12 days after infection.

Compared with the control plants, infestation of the plants treated with compounds of formula I from Tables 1–7, for example the compounds 1.36, 2.30, 3.1, 3.6, 3.8, 3.15, 3.17, 3.26, 3.30, 3.31, 3.34, 3.36, 3.47, 3.52, 3.56, 3.58, 3.59, 3.79, 3.117, 3.118, 3.163, 3.171, 4.36, 6.29, 7.6, 7.31 and 7.34 is 20% or less.

Example B-4
Action Against *Podosphaera leucotricha* on Apple Shoots

Apple cuttings with fresh shoots about 15 cm long are sprayed with a spray mixture (0.06% a.i.). The plants are infected 24 hours later with a conidia suspension of the fungus and stood in a climatic chamber at 70% relative humidity and 20° C. Evaluation of the fugal infestation is made 12 days after infection.

Compounds of Tables 1–7 show good activity. The following compounds exhibit especially strong efficacy: 1.36, 2.30, 3.1, 3.6, 3.8, 3.15, 3.17, 3.26, 3.30, 3.31, 3.34, 3.36, 3.47, 3.52, 3.56, 3.58, 3.59, 3.79, 3.117, 3.118, 3.163, 3.171, 4.36, 6.29, 7.6, 7.31 and 7.34 (0–5% infestation).

Example B-5
Action Against *Plasmopara viticola* on Vines
a) Residual-preventive action: Vine cuttings of the Chasselas variety are raised in a greenhouse. At the 10-leat stage, 3 plants are sprayed with a spray mixture (200 ppm a.i.). After the spray coating has dried, the plants are infected uniformly on the underside of the leaves with a spore suspension of the fungus. The plants are then kept in a humidity chamber for 8 days, after which time marked symptoms of disease are observed on the control plants. The number and size of the infected areas on the untreated plants act as an indicator of the efficacy of the tested compounds.

b) Curative action: Vine cuttings of the Chasselas variety are raised in a greenhouse and sprayed at the 10-leaf stage on the underside of the leaves with a spore suspension of Plasmopara viticola. After 24 hours in the humidity chamber, the plants are sprayed with a spray mixture (200 ppm a.i.). The plants are then kept for another 7 days in the humidity chamber. After this time the control plants exhibit symptoms of the disease. The number and size of the infected areas on the untreated plants act as an indicator of the efficacy of the tested compounds.

Compounds of Tables 1–7 show good efficacy, preferably the compounds 1.36, 2.30, 3.1, 3.6, 3.8, 3.15, 3.17, 3.26, 3.30, 3.31, 3.34, 3.36, 3.47, 3.52, 3.56, 3.58, 3.59, 3.79, 3.117, 3.118, 3.163, 3.171, 4.36, 6.29, 7.6, 7.31 and 7.34.

Example B-6
Action Against *Uncinula necator* on Vines 5 week old vine cuttings are sprayed with a spray mixture (200 ppm a.i.) prepared from a wettable powder formulation of the test compound. The plants are infected 24 hours later by conidias from strongly infested vine leafs that are shaken off over the test plants. The plants are then incubated at 26° C. and 60% relative humidity. The evaluation of the fungal infestation is made ca. 14 days after infection.

Compared with the control plants, infestation of the plants treated with compounds of formula I from the Tables 1–7, for example the compounds 1.36, 2.30, 3.1, 3.6, 3.8, 3.15, 3.17, 3.26, 3.30, 3.31, 3.34, 3.36, 3.47, 3.52, 3.56, 3.58, 3.59, 3.79, 3.117, 3.118, 3.163, 3.171, 4.36, 6.29, 7.6, 7.31 and 7.34 is 20% or less.

What is claimed is:

1. A compound of formula I

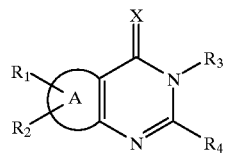

(I)

wherein

A is thienyl (including all 3 isomers):

X is oxygen or sulfur;

$R_1$ is hydrogen, halogen or trimethylsilyl;

$R_2$ is hydrogen, halogen or trimethylsilyl; at least one of $R_1$ and $R_2$ is not hydrogen;

$R_3$ is $C_1$–$C_8$alkyl, $C_1$–$C_8$alkenyl, $C_1$–$C_8$alkynyl which are unsubstituted or mono to tri-substituted by $C_3$–$C_6$cycloalkyl, halogen, $C_1$–$C_6$alkoxy or $C_1$–$C_6$haloalkoxy, O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_6$alkoxy; N—$C_1$–$C_6$alkyl: or N=CH$C_1$–$C_6$alkyl;

$R_4$ is $C_1$–$C_8$alkyl, $C_1$–$C_8$alkenyl, $C_1$–$C_8$alkynyl which are unsubstituted or mono to tri-substituted by $C_3$–$C_8$cycloalkyl, halogen, cyano, $C_1$–$C_6$alkoxy or $C_1$–$C_8$ahaloalkoxy; nitro; —CO—$C_1$–$C_8$alkyl; $C_3$–$C_6$cycloalkyl; or phenyl, which is unsubstituted or mono to tri-substituted by halogen, $C_1$–$C_6$alkyl, $C_1$–$C_6$haloalkyl, $C_1$–$C_6$alkoxy, $C_1$–$C_6$haloalkoxy, cyano, nitro, amino, mono-$C_1$–$C_6$alkylamino, di-$C_1$–$C_6$alkylamino, $C_1$–$C_8$alkylthio, phenyl or phenoxy and in which the phenyl part is unsubstftuted or mono to tri-substituted by halogen, $C_1$–$C_6$alkyl, $C_1$–$C_6$haloalkyl, $C_1$–$C_6$alkoxy or $C_1$–$C_6$haloalkoxy.

2. A compounds of formula I according to claim 1 wherein $R_1$ is hydrogen, fluorine, chlorine, bromine or iodine;

$R_2$ is hydrogen, fluorine, chlorine, bromine or iodine, at least one of $R_1$ anld $R_2$ is not hydrogen;

$R_3$ is $C_1$–$C_6$alkyl, $C_2$–$C_6$alkenyl, $C_1$–$C_6$alkynyl which are unsubstituted or mono to tri-substituted by $C_3$–$C_6$cycloalky, halogen or $C_1$–$C_4$alkoxy; O—$C_1$–$C_6$alkyl, O—$C_2$–$C_6$alkenyl, O—$C_2$–$C_6$alkynyl, which are unsubstituted or mono to tri-substituted by $C_1$–$C_6$cycloalkyl, halogen or $C_1$–$C_4$alkoxy; N—$C_1$–$C_6$alkyl; or N=CH$C_1$–$C_6$alkyl;

$R_4$ is $C_1$–$C_6$alkyl, $C_2$–$C_6$alkenyl, $C_1$–$C_6$alkynyl which are unsubstituted or mono to tri-substituted by $C_1$–$C_6$cycloalkyl, halogen or $C_1$–$C_4$alkyoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$haloalkoxy, phenyl or phenoxy and in which the phenyl part is unsubstituted or mono to tri-substituted by fluorine, chlorine, bromine, $C_1$–$C_4$alkyl, $C_1$–$C_4$haloalkyl, $C_1$–$C_4$alkoxy or $C_1$–$C_4$haloalkoxy.

3. A compound of formula I according to claim 2, wherein $R_3$ is $C_1$–$C_6$alkyl, $C_2$–$C_6$alkenyl, $C_2$–$C_6$alkynyl which are unsubstituted or mono to tri-substituted by $C_3$–$C_4$cycloalkyl, fluorine, chlorine, bromine or $C_1$–$C_4$alkoxy; O—$C_1$–$C_6$alkyl; O—$C_2$–$C_6$alkenyl; O—$C_2$–$C_6$alkynyl: N—$C_1$–$C_6$alkyl; or N=CH$C_1$–$C_6$alkyl;

$R_4$ is $C_1$–$C_6$alkyl, $C_2$–$C_6$alkenyl, $C_2$–$C_6$alkynyl which are unsubstituted or manno to tri-substituted by $C_3$–$C_4$cycloalkyl, fluorine, chlorine, bromine or $C_1$–$C_4$alkoxy; or phenyl which is unsubstituted or mono to tri-substituted by fluorine, chlorine, bromine, $C_1$–$C_4$alkyl, $C_1$–$C_4$haloalkyl, $C_1$–$C_4$alkoxy, $C_1$–$C_4$halo-alkoxy, phenyl or phenoxy and in which the phenyl part is unsubstituted or mono to tri-substituted by fluorine, chlorine or bromine.

4. A compound of the formula I according to claim 3, wherein

A is thienyl[2.3-d],

X is oxygen, $R_1$ is hydrogen, chlorine or bromine;

$R_2$ is hydrogen, chlorine or bromine; at least one of $R_1$ and $R_2$ is not hydrogen;

$R_3$ is $C_3$–$C_5$alkyl or O—$C_1$–$C_4$alkyl;

$R_4$ is $C_2$–$C_5$alkyl or phenyl which is unsubstituted or mono to tri-substituted by fluorine, chlorine, bromine, $C_1$–$C_4$alkyl or phenoxy and in which phenoxy is unsubstituted or mono to tri-substituted by fluorine, chlorine or bromine.

5. A compound of the formula I according to claim 3, wherein

A is thienyl[2.3-d],

X is sulfur, $R_1$ is hydrogen, chlorine or bromine;

$R_2$ is hydrogen, chlorine or bromine; at least one of $R_1$ and $R_2$ is not hydrogen;

$R_3$ is $C_3$–$C_5$alkyl or O—$C_1$–$C_4$alkyl;

$R_4$ is $C_1$–$C_5$alkyl or phenyl which is unsubstituted or mono to tri-substituted by fluorine, chlorine, bromine, $C_1$–$C_4$alkyl or phenoxy and in which phenoxy is unsubstituted or mono to tri-substituted by fluorine, chlorine or bromine.

6. A compound of the formula I according to claim 3, wherein

A is thienyl[3.2-d],

X is oxygen, $R_1$ is hydrogen, chlorine or bromine;

$R_2$ is hydrogen, chlorine or bromine; at least one of $R_1$ and $R_2$ is not hydrogen;

$R_3$ is $C_3$–$C_5$alkyl or O—$C_1$–$C_4$alkyl;

$R_4$ is $C_2$–$C_5$alkyl or phenyl which is unsubstituted or mono to tri-substituted by fluorine, chlorine, bromine, $C_1$–$C_4$alkyl or phenoxy and in which phenoxy is unsubstituted or mono to tri-substituted by fluorine, chlorine or bromine.

7. A composition for controlling and preventing pests, wherein the active ingredient is a compound as claimed in claim 1 together with a suitable carrier.

8. A method of controlling or preventing infestation of cultivated plants by phytopathogenic microorganisms by application of a compound of formula I as claimed in claim 1 to plants, to parts thereof or to the locus thereof.

9. A method according to claim 8 wherein the phytopathogenic microorganism is a fungal organism.

10. A method for the preparation of a compound of formula I according to claim 1, which comprises a) converting an α-amino-β-carboalkoxyheterocycle of formula II, wherein $R_1$ and $R_2$ have the meanings stated for formula I and R is hydrogen, $C_1$–$C_6$alkyl,

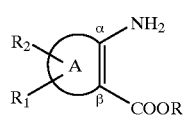

with $POCl_3$ in the presence of a solvent and $R_4CONHR_3$ into an amidine of formula III, wherein $R_3$ and $R_4$ have the meanings stated for formula I

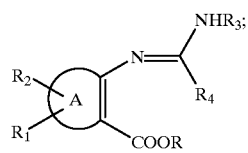

b) and treating the amidine, in the presence of a solvent and in the presence or absence of a base, and obtaining, with ring closure, the pyrimidin-4-one derivative of formula IV

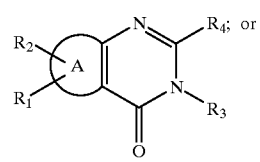

c) reacting an amino carboxylic acidamide of formula VI

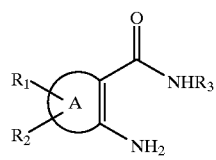

wherein A, $R_1$, $R_2$ and $R_3$ have the meanings stated for formula I with an orthoester of formula XIII

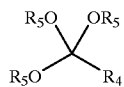

wherein $R_4$ has the meaning stated for formula I and $R_5$ is $C_1$–$C_5$alkyl, in the presence or absence of a solvent, in the presence or absence of an acid catalyst at 20–200° C., and obtaining the pyrimidin-4-one derivative of formula IV; and d) If the intermediate VII is formed

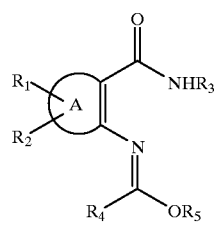

treating the compound VII in the presence of a solvent and in the presence or absence of a base, and obtaining with ring closure the pyrimidin-4one derivative of formula IV.

11. A compound of formula III

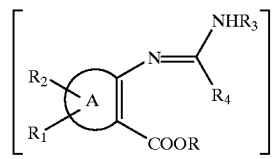

wherein
A is thienyl[2.3-d] or thienyl[3.2-d];
$R_1$ is hydrogen, halogen or trimethylsilyl;
$R_2$ is hydrogen, halogen or trimethylsilyl; and at least one of $R_1$ and $R_2$ is not hydrogen;
$R_3$ is $C_1$–$C_8$alkyl, $C_1$–$C_8$alkenyl, $C_1$–$C_8$alkynyl which are unsubstituted or mono to tri-substituted by $C_3$–$C_6$cycloalkyl, halogen, $C_1$–$C_6$alkoxy or $C_1$–$C_6$haloalkoxy; O—$C_1$–$C_6$alkyl, O—$C_2$–$C_6$alkenyl, O—$C_2$–$C_6$alkynyl, which are unsubstituted or mono to tri-substituted by $C_3$–$C_6$cycloalkyl, halogen or $C_1$–$C_6$alkoxy; N—$C_1$–$C_6$alkyl; or N=CH$C_1$–$C_6$alkyl;
$R_4$ is $C_1$–$C_8$alkyl, $C_1$–$C_8$alkenyl, $C_1$–$C_8$alkynyl which are unsubstituted or mono to tri-substituted by $C_3$–$C_6$cycloalkyl, halogen, cyano, $C_1$–$C_6$alkoxy or $C_1$–$C_6$haloalkoxy; nitro; —CO—$C_1$–$C_6$alkyl; $C_3$–$C_6$cycloalkyl; or phenyl, which is unsubstituted or mono to tri-substituted by halogen, $C_1$–$C_6$alkyl, $C_1$–$C_6$haloalkyl, $C_1$–$C_6$alkoxy, $C_1$–$C_6$haloalkoxy, cyano, nitro, amino, mono-$C_1$–$C_6$alkylamino, di-$C_1$–$C_6$alkyl-amino, $C_1$–$C_6$alkylthio, phenyl or phenoxy and in which the phenyl part is unsubstituted or mono to tri-substituted by halogen, $C_1$–$C_6$alkyl, $C_1$–$C_6$haloalkyl, $C_1$–$C_6$alkoxy or $C_1$–$C_6$halo-alkoxy, and
R is hydrogen or $C_1$–$C_6$alkyl.

* * * * *